US006258557B1

(12) United States Patent
Lee et al.

(10) Patent No.: US 6,258,557 B1
(45) Date of Patent: *Jul. 10, 2001

(54) SMOOTH MUSCLE CELL LIM PROMOTER

(75) Inventors: Mu-En Lee, Newton, MA (US); Edgar Haber, Salisbury, NH (US); Mukesh Jain, West Newton; Shaw-Fang Yet, Andover, both of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/818,655

(22) Filed: Mar. 14, 1997

Related U.S. Application Data

(63) Continuation-in-part of application No. 08/616,368, filed on Mar. 15, 1996, now Pat. No. 5,767,262.

(51) Int. Cl.$^7$ .......................... C12N 15/63; C12N 15/09; C12N 15/00; C12N 5/00

(52) U.S. Cl. .................... 435/69.1; 435/320.1; 435/325; 435/455; 435/6; 536/23.1; 536/23.5; 536/24.31; 514/44

(58) Field of Search .................................. 536/23.1, 23.5, 536/24.31; 435/320.1, 325, 455, 6, 69.1; 514/44

(56) References Cited

U.S. PATENT DOCUMENTS 5,585,479 * 12/1996 Hoke et al. ......................... 536/24.5

OTHER PUBLICATIONS

Arber et al., "Muscle LIM Protein, a Novel Essential Regulator of Myogenesis, Promotes Myogenic Differentiation", *Cell*, 79:221–31 (1994).
Bredt et al., "Localizaton of nitric oxide synthase indicating a neural role for nitric oxide," *Nature*, 347:768–70 (1990).
Crawford et al., "Biochemical and Molecular Characterization of the Chicken Cysteine–rich Protein, a Developmentally Regulated LIM–Domain Protein That Is Associated with the Actin Cytoskeleton", *J. Cell Biol.*, 124:117–27 (1994).
Doetschman et al., "The in vitro development of blastocyst–derived embryonic stem cell lines: formation of visceral yolk sac. blood islands and myocardium," *J. Embroyol. Exp. Morph.*, 87:27–45 (1985).
El Deiry et al., "WAF1, a Potential Mediator of p 53 Tumor Suppression," *Cell*, 75:817–23 (1993).
Lee et al., " The Type I Iodothyronine 5'–Deiodinase Messenger Ribonucleic Acid Is Localized to the S3 Segment of the Rat Kidney Proximal Tubule," *Endocrinology*, 132:2136–40 (1993).
Libby et al., "Biology of Disease: Involvement of the Immune System in Human Atherogenesis: Current Knowledge and Unanswered Questions", *Lab. Investig.*, 64:5–15 (1991).

Liebhaber et al., "Characterization of a Human cDNA Encoding a Widely Expressed and Highly Conserved Cysteine–rich Protein with an Unusual Zinc–finger Motif", *Nucleic Acids Research*, 18:3871–79 (1990).
Melani et al., "Characterization of a human cDNA encoding a widely expressed and highly conserved cysteine–rich protein with an unusual zinc–finger motif," *Cancer Res.*, 51:2897–901 (1991).
Munro et al., "Biology of Disease: The Pathogenesis of Atherosclerosis: Atherogenesis and Inflammation", *Lab. Invest.*, 58:249–61 (1988).
Pennica et al., "Cloning and expression of human tissue–type plasminogen activator cDNA in *E. coli,* " *Nature*, 301:214 (1982).
Ross, "The Pathogenesis of Atherosclerosis: a Perspective for the 1990s", *Nature*, 362:801–809 (1993).
Sadler et al., "Zyxin and cCRP: Two Interactive LIM Domain Proteins Associated with the Cytoskeleton", *J. Cell Biol.*, 119:1573–87 (1992).
Tsai et al., "Promotion of Vascular Smooth Muscle Cell Growth by Homocysteine: A Link to Atherosclerosis", *PNAS USA*, 91:6369–73 (1994).
Tsai et al., "Induction of Cyclin A Gene Expression by Homocysteine in Vascular Smooth Muscle Cells", *J. Clin. Invest.*, 97:146–53 (1996).
Wang et al., "Analysis of the Human Cysteine–Rich Protein Gene (CSRP) Assignment to Chromosome 1q24–1q32, and Identification of an Associated Mspl Polymorphism", *Genomics*, 14:391–97 (1992).
Wang et al., "Human Cysteine–rich Protein: A Member of the Lim/Double–Finger Family Displaying Coordinate Serum Induction with c–myc", *J. Biol. Chem.*, 267:9176–84 (1992).
Warren et al., "The Oncogenic Cysteine–Rich LIM Domain Protein Rbtn2 is Essential for Erythroid Development" *Cell*, 78: 45–57 (1994).
Weiskirchen et al., "The Cysteine–rich Protein Family of Highly Related LIM Domain Proteins", *J. Biol. Chem.* 270:28946–54 (1995).
Weiskirchen et al., "Suppression in Transformed Avian Fibroblasts of a Gene (crp) Encoding a Cysteine–rich Protein Containing LIM Domains", *Oncogene* 8:2317–24 (1993).
Williams et al., "Introduction of foreign genes into tissues of living mice by DNA–coated microprojectiles," *PNAS USA*, 88:2726–29 (1991).
Hillier et al., yw62f09.rl Homo sapiens cDNA clone 256841 5' similar to gb: M33146 Cysteine–Rich Protein (Human), GenBank Accession # N39473, Jan. 19, 1996.

* cited by examiner

*Primary Examiner*—Jill D. Martin
(74) *Attorney, Agent, or Firm*—Ivor R. Elrifi; Ingrid A. Beattie; Mintz, Levin, Cohn, Ferris, Glovsky and Popeo, P.C.

(57) ABSTRACT

The invention provides an isolated DNA which regulates vascular smooth muscle cell-specific transcription of a polypeptide-encoding sequence to which it is operably linked

16 Claims, 8 Drawing Sheets

HOECHST 33258

9E10

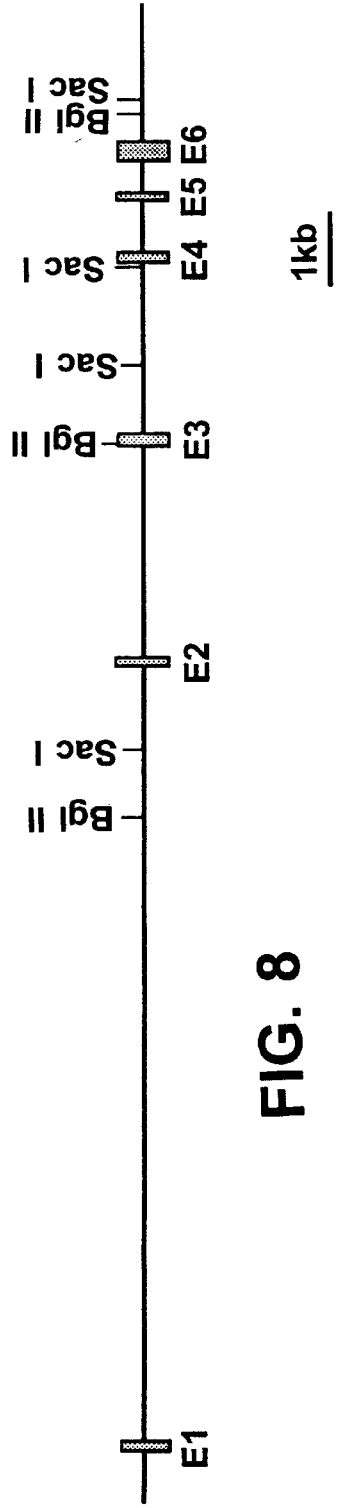

FIG. 8

```
-438  TGAGGAATGCAGCTCTTTCGCGACAGGAAAGCTGCGGATTCCAGAAGCCGGGATTCTGAC
                                                    E-box
-378  CAGAGACTATCCTGCACCGGGAGTCCTGCACCCCGGAGGCTAACATATGGCGTTTGTGC
            CACCC-box/Sp1/NFκB           CACCC-box
-318  AGTAAAGGGTGGCGGGAATCCCACGGGGCGACACCGGATCTCGCTGGCTCCGGGCCGATC
                                                        C/EBP
-258  CTGAGTGCTCCCGGACGCGTCCCGGACCGCGGGTAGGAGCAGCCGAGACGTGGGAGACTCGG
                                         Sp1
-198  ACGCGCGGAAGCCGCGAGAAGAGACGGATTCCGGTCTTTTGTCTCGGGGCCAGAGCTC
                                              Sp1              CACCC-box
-138  GAAACCCGCAGCGGGAGCCCAGCTCAGCGGGGCCGGGCGGAGACCATCGCACACCCCGAG
                                 Sp1          Sp1
 -78  GGGCATGACCGATGATGGGCGTGGCGAACAAGGCCACGCCCAACATAAGTCTTTAAAAGC
                 ↑      Sp1/AP2
 -18  GGGCACACGCGTCCCGCCAGTCTCCGCCGATCCGCCCGCGGCTTTCCTCGGTCAGACCTCGT
      Sp1/AP2                                          CACCC-box
 +43  TAGCTCCGCCGCCGCGTGCTCCCCTGCTCCCCTCCCCCCACTCGGgtgagtcctaggctc (SEQ ID NO: 16)
```

FIG. 9

SMOOTH MUSCLE CELL LIM PROMOTER

CROSS REFERENCE TO RELATED APPLICATION

This application is a continuation-in-part of U.S. patent application Ser. No. 08/616,368, filed on Mar. 15, 1996, now U.S. Pat. No. 5,767,262, the contents of which is hereby incorporated by reference.

STATEMENT AS TO FEDERALLY SPONSORED RESEARCH

This invention was made with U.S. Government support under National Institutes of Health grant RO1 GM53249. The government has certain rights in the invention.

BACKGROUND OF THE INVENTION

The invention relates to diagnosis and treatment of vascular injury.

In their normal state, vascular smooth muscle cells regulate vessel tone and blood pressure. Unlike skeletal muscle and cardiac muscle cells, these cells are not terminally differentiated. In response to mechanical, chemical, or immunologic injury (Libby et al., 1991, Lab Invest. 64:5–15; Munro et al., 1988, Lab Invest. 58:249–261; Ross, R., 1993, Nature 362:801–809; Tsai et al., 1994, Proc. Natl. Acad. Sci. USA 91:6369–6373; and Tsai et al., 1996, Clin. Invest. 97:146–153), the phenotype of these cells changes rapidly from that of a differentiated, quiescent cell to that of a dedifferentiated, proliferating cell. Although vascular smooth muscle cell proliferation is a hallmark of arteriosclerosis, the leading cause of death in developed countries, little is known about the molecular mechanisms regulating this phenotypic change.

SUMMARY OF THE INVENTION

The invention is based on the identification and characterization of a smooth muscle cell LIM (SmLIM/CRP2) polypeptide which is expressed preferentially in arterial smooth muscle cells. SmLIM/CRP2 expression was found to decrease as vascular smooth muscle cells changed from a quiescent, differentiated phenotype to a proliferative phenotype in response to vascular injury.

The invention features a substantially pure DNA containing a sequence which encodes a SmLIM/CRP2 polypeptide. By the term "SmLIM/CRP2" is meant a polypeptide that contains at least two LIM domains, lacks a homeobox domain and a protein kinase domain, and inhibits proliferation of vascular smooth muscle cells. By "substantially pure DNA" is meant DNA that is free of the genes which, in the naturally-occurring genome of the organism from which the DNA of the invention is derived, flank the SmLIM/CRP2 gene. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. A "LIM domain" is defined by the amino acid consensus sequence $CX_2CX_{17\pm1}HX_2CX_2CX_2CX_{17\pm1}CX_2C/D/H$ (SEQ ID NO:18).

The SmLIM/CRP2 polypeptide of the invention preferably has at least 85% sequence identity with SEQ ID NO:1, and more preferably at least 90% (e.g., at least 95%). The DNA may encode a naturally occurring mammalian SmLIM/CRP2 polypeptide such as a human, rat, mouse, guinea pig, hamster, dog, cat, pig, cow, goat, sheep, horse, monkey, or ape SmLIM/CRP2. For example, the SmLIM/CRP2 polypeptide may have the amino acid sequence of the naturally-occurring human polypeptide, e.g., a polypeptide which includes the amino acid sequence of SEQ ID NO:1. Preferably, the DNA includes the nucleotide sequence of SEQ ID NO:2. The DNA may contain a strand which hybridizes at high stringency to a DNA probe having a portion or all of the nucleotide sequence of SEQ ID NO:2, or the complement thereof. The probe to which the DNA of the invention hybridizes preferably consists of at least 20 nucleotides, more preferably 40 nucleotides, even more preferably 50 nucleotides, and most preferably 100 nucleotides or more (up to 100%) of the nucleotide sequence of SEQ ID NO:2, or the complement thereof. Such a probe is useful for detecting expression of a SmLIM/CRP2 transcript in a cell by a method which includes the steps of (a) contacting mRNA obtained from the cell with the labeled hybridization probe; and (b) detecting hybridization of the probe with the mRNA transcript. The invention also includes a substantially pure strand of DNA containing at least 15 nucleotides (preferably 20, more preferably 30, even more preferably 50, and most preferably all) of SEQ ID NO:2.

Hybridization is carried out using standard techniques such as those described in Ausubel et al., *Current Protocols in Molecular Biology*, John Wiley & Sons, (1989). "High stringency" refers to DNA hybridization and wash conditions characterized by high temperature and low salt concentration, e.g., wash conditions of 65° C. at a salt concentration of approximately 0.1×SSC. "Low" to "moderate" stringency refers to DNA hybridization and wash conditions characterized by low temperature and high salt concentration, e.g. wash conditions of less than 60° C. at a salt concentration of at least 1.0×SSC. For example, high stringency conditions may include hybridization at about 42° C., and about 50% formamide; a first wash at about 65° C., about 2×SSC, and 1% SDS; followed by a second wash at about 650° C. and about 0.1%×SSC. Lower stringency conditions suitable for detecting DNA sequences having about 50% sequence identity to a SmLIM/CRP2 gene are detected by, for example, hybridization at about 42° C. in the absence of formamide; a first wash at about 42° C., about 6×SSC, and about 1% SDS; and a second wash at about 50° C., about 6×SSC, and about 1% SDS.

The invention also includes a substantially pure DNA encoding a SmLIM/CRP2 polypeptide, which DNA includes a nucleotide sequence having at least 50% sequence identity to SEQ ID NO:2. Preferably the DNA has at least 70%, more preferably at least 80%, more preferably at least 90%, more preferably at least 95%, and most preferably at least 99% identity to SEQ ID NO:2. The percent sequence identity of one DNA to another is determined by standard means, e.g., by the Sequence Analysis Software Package developed by the Genetics Computer Group (University of Wisconsin Biotechnology Center, Madison, Wis.) (or an equivalent program), employing the default parameters thereof.

The DNA may be operably linked to regulatory sequences, e.g., a promoter, for expression of the polypeptide. Preferably, the promoter is vascular cell-specific, more preferably, it is vascular smooth muscle cell-specific, and most preferably, it is arterial smooth muscle cell-specific. By "operably linked" is meant that a coding sequence and a regulatory sequence(s) are connected in such a way as to permit gene expression when the appropriate molecules (e.g., transcriptional activator proteins) are bound to the regulatory sequence(s). By "promoter" is meant a minimal DNA sequence sufficient to direct transcription. Promoters may be constitutive or inducible.

The invention includes a substantially pure DNA containing a sequence at least 50% identical to SEQ ID NO:3 or SEQ ID NO:16, which regulates arterial smooth muscle cell-specific transcription of a polypeptide-encoding sequence to which it is operably linked. Preferably, the DNA is at least 75% identical, more preferably at least 90% identical, more preferably at least 95%, and most preferably 100% identical to SEQ ID NO:3 or SEQ ID NO:16. The DNA may be operably linked to a heterologous polypeptide-encoding sequence and may be used in a method of directing arterial smooth muscle cell-specific expression of the polypeptide, e.g., by introducing the DNA linked to the coding sequence into an arterial cell. By the term "heterologous polypeptide" is meant a polypeptide other than a SmLIM/CRP2 polypeptide.

The invention also includes a substantially pure DNA comprising a first DNA sequence containing a SmLIM/CRP2-derived promoter sequence, e.g., one which is at least 50% identical to SEQ ID NO:3 or 16, operably linked to a second DNA sequence encoding a polypeptide other than SmLIM/CRP2, i.e., a heterologous peptide, wherein the first DNA sequence directs transcription of the second DNA sequence preferentially in an a vascular smooth muscle cell, e.g., an arterial smooth muscle cell, compared to in a non-vascular smooth muscle cell. Preferably, the second DNA sequence does not encode SmLIM/CRP2. Vascular smooth muscle cell-specific expression of a polypeptide is accomplished by introducing into an vascular smooth muscle cell a vector containing SmLIM promoter sequences operably linked to polypeptide-encoding DNA and maintaining the cell under conditions suitable for expression of the second DNA, e.g., in vitro culture under standard tissue culture conditions or in vivo, i.e., in an animal. For example, the invention provides a method of inhibiting arteriosclerosis in an animal by contacting an artery of an animal with the vector containing DNA encoding a polypeptide which reduces or prevents the development of arteriosclerosis. e.g., a polypeptide which reduces proliferation of smooth muscle cells.

Alternatively, the second DNA sequence may be a an antisense template the transcript of which is complementary to a portion of an mRNA encoding a vascular smooth muscle cell polypeptide. Thus, the invention includes a substantially pure DNA comprising a first DNA sequence containing a SmLIM/CRP2-derived promoter sequence, e.g, one which is at least 50% identical to SEQ ID NO:3 or 16, operably linked to a second DNA sequence which is an antisense template the transcript of which is complementary to a portion of an mRNA encoding an vascular smooth muscle cell polypeptide. The first DNA sequence directs transcription of the second DNA sequence preferentially in a vascular smooth muscle cell compared to in a non-vascular smooth muscle cell. By the term "antisense template" is meant a DNA which is transcribed into an RNA which hybridizes to mRNA encoding a polypeptide expressed in vascular smooth muscle cells.

Preferably the level of transcription of a polypeptide-encoding or antisense template in vascular smooth muscle cells under the control of a SmLIM/CRP2-derived promoter sequence is at least 2-fold greater, more preferably 3-fold, more preferably 4-fold, and more preferably 10-fold greater than that in non-vascular smooth muscle cells. Most preferably, the SmLIM/CRP2-derived promoter sequence of the invention direct vascular smooth muscle cell-specific transcription of the DNA to which it is linked.

The invention also includes a vector containing the promoter sequences of the invention, a method of directing vascular smooth muscle cell-specific expression of a polypeptide by introducing the vector into an vascular smooth muscle cell, and a vascular smooth muscle cell containing the vector.

The vector of the invention can be used for gene therapy, such as a method of inhibiting arteriosclerosis in an animal by contacting an artery of the animal with the vector of the invention which directs the production of a polypeptide capable of reducing or preventing the development of arteriosclerosis.

A cell which contains a recombinant SmLIM/CRP2 polypeptide-encoding DNA is also within the invention. The cell may be eucaryotic or procaryotic. A method of making a SmLIM/CRP2 polypeptide includes the steps of (a) providing the cell which contains SmLIM/CRP2 polypeptide-encoding DNA, and (b) culturing it under conditions permitting expression of the DNA. If the polypeptide is secreted by the cell, the SmLIM/CRP2 polypeptide produced can be recovered from the culture supernatant of the cell culture. If the polypeptide is not secreted, the polypeptide can be recovered by lysing the cultured cells.

The invention also includes a substantially pure human SmLIM/CRP2 polypeptide. Preferably, the amino acid sequence of the polypeptide is at least 90% identical, more preferably at least 95% identical, more preferably at least 99% identical to the amino acid sequence of SEQ ID NO:1. Most preferably, the amino acid sequence of the polypeptide includes SEQ ID NO:1. By a "substantially pure polypeptide" is meant a polypeptide which is separated from those components (proteins and other naturally-occurring organic molecules) which naturally accompany it. Typically, the polypeptide is substantially pure when it constitutes at least 60%, by weight, of the protein in the preparation. Preferably, the protein in the preparation consists of at least 75%, more preferably at least 90%, and most preferably at least 99%, by weight, a SmLIM/CRP2 polypeptide. A substantially pure SmLIM/CRP2 polypeptide may be obtained, for example, by extraction from a natural source (e.g., an arterial smooth muscle cell); by expression of a recombinant nucleic acid encoding a SmLIM/CRP2 polypeptide; or by chemically synthesizing the protein. Purity can be measured by any appropriate method, e.g., column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components even without further purification steps. Accordingly, substantially pure polypeptides include recombinant polypeptides derived from a eucaryote but produced in *E. coli* or another procaryote, or in a eucaryote other than that from which the polypeptide was originally derived.

The invention also includes diagnostic methods. For example, one can detect injury in a sample of vascular tissue by determining the level of SmLIM/CRP2 gene expression in the tissue sample, and comparing it to the level of expression in a control sample of vascular tissue. This determination may be made using SmLIM/CRP2-specific DNA probes to detect the level of gene transcription or using SmLIM/CRP2-specific antibodies to detect the level of gene product in the cells. A decrease in the level of expression of SmLIM/CRP2 compared to the level in uninjured control vascular tissue indicates the presence of a vascular injury.

Methods of therapy are also within the invention. A method of inhibiting arterial smooth muscle cell proliferation in a mammal may include the steps of identifying a mammal in need of such inhibition, and introducing either SmLIM/CRP2 or a SmLIM/CRP2-encoding DNA into an artery of the mammal. One can inhibit neointima formation after balloon angioplasty in a mammal by contacting an artery of the mammal with a SmLIM/CRP2 or SmLIM/CRP2-encoding DNA prior to, during, or immediately after angioplasty to reduce proliferation of arterial smooth muscle cells in the mammal, particularly at the site of vascular injury treated by the angioplasty procedure. Preferably, the mammal is a human, and the SmLIM/CRP2 polypeptide is a human SmLIM/CRP2 polypeptide.

A method of screening candidate compounds to identify a compound capable of increasing expression of a SmLIM/CRP2 polypeptide in vascular smooth muscle cells is also within the invention. For example, an in vitro method may include the steps of (a) providing a vascular smooth muscle cell, e.g., a human arterial smooth muscle cell; (b) contacting the smooth muscle cell with a candidate compound; and (c) determining the amount of SmLIM/CRP2 expression by the vascular smooth muscle cell. The screening method can also be carried out in vivo, e.g., in an animal subjected to a vascular injury, and then treated with the candidate compound or a placebo. An increase in the amount of expression in the presence of the candidate compound compared to that in the absence of the candidate compound indicates that the candidate compound increases expression of a SmLIM/CRP2 polypeptide in vascular smooth muscle cells. An increase of SmLIM/CRP2 expression correlates with an inhibition in vascular smooth muscle cell proliferation. Expression may be determined by measuring gene transcription, e.g., in a Northern blot assay, or by measuring the amount of SmLIM/CRP2 polypeptide in the cell, e.g., by immunoblotting.

Other features and advantages of the invention will be apparent from the following detailed description, and from the claims.

BRIEF DESCRIPTION OF THE DRAWINGS

FIG. 8 is a diagram showing the structural organization and partial restriction map of the gene encoding mouse SmLIM/CRP2. Exons are shown as filled rectangles.

FIG. 9 is a diagram of a SmLIM-CRP2 promoter sequence (SEQ ID NO:16) in which cis-acting transcriptional regulatory sequences are indicated above the DNA sequence. The DNA sequence is numbered on the left. Cis-acting sequences are underlined. A TATA-like sequence is in boldface. The transcriptional start site is marked by a bent arrow, and intron 1 sequences are in lower case.

DETAILED DESCRIPTION

Cell Culture and Reagents

Figure 1:
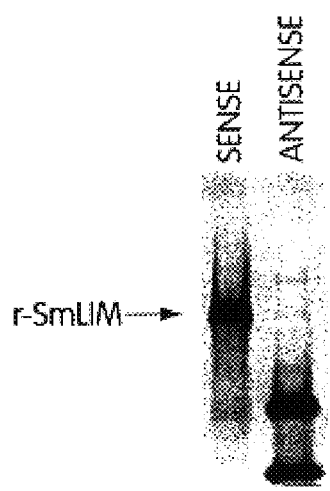
FIG. 1 is a photograph of an sodium dodecyl sulfate-polyacrylamide gel electrophoresis (SDS-PAGE) analysis of proteins. The entire rat (r-SmLIM/CRP2) open reading frame was cloned in the sense and antisense orientations into the eucaryotic expression vector PCRIII. After in vitro transcription and translation with wheat germ lysate, the protein was resolved on a 10% SDS-PAGE Tricine gel. The single intense band in the sense lane (arrow) represents full-length SmLIM/CRP2 at 21 kDa.

Aortic smooth muscle cells were harvested from the thoracic aorta of adult male Sprague-Dawley rats (200–250 g) by enzymatic digestion. COS-7 (CRL 1651) and 10T1/2 (CCL 226) cells were obtained from the American Type Cell Culture Collection. Rat aortic smooth muscle cells were grown in DME medium (JRH Biosciences, Lenexa, Kans.) supplemented with 10% FCS, penicillin (100 U/ml), streptomycin (100 μg/ml), and 25 mM Hepes (pH 7.4) in a humidified incubator (37° C., 5% $CO_2$). COS-7 and 10T1/2 cells were grown similarly, with the exceptions that DME was supplemented with Serum Plus (Hyclone, Logan, Utah) for the former and BME (JRH Biosciences) was substituted for DME for the latter. Embryonic stem cells (D3) were cultured using known methods. Cells were cultured and maintained in an undifferentiated state with leukemia inhibitory factor using known methods, e.g., Doetschman et al., 1985, J. Embryol. Exp. Morph. 87:27–45. PDGF-BB was purchased from Collaborative Biomedical Products (Bedford, Mass.).

Cloning and Sequencing of r-SmLIM/CRP2, Mouse SmLIM/CRP2 (m-SmLIM/CRP2) and h-SmLIM/CRP2

The full-length rat muscle LIM protein (MLP) cDNA was amplified from rat heart RNA by the reverse transcriptase PCR. Forward (5'GAGTCTTCACCATGCCGAAC3' SEQ ID NO:4) and reverse (5'CTCTCCCACCCCAAAATAG3' SEQ ID NO:5) primers, designed according to the published rat MLP sequence (Arber et al., 1994, Cell 79:221–231), were used to amplify a 801-bp fragment. The PCR fragment was then subcloned and sequenced by the dideoxy chain termination method. The rat-MLP fragment was used to screen a rat neonatal aortic cDNA library in λgt11. Approximately 1.6 million phage clones were plated, transferred to nitrocellulose paper, and screened at low stringency. One out of nine isolated clones encoded the partial sequence of a novel LIM protein, r-SmLIM/CRP2. This partial clone was then used to screen a rat smooth muscle cDNA library in λZAP (Clontech) to obtain the full-length clone. The same partial rat clone was also used to screen a human aortic λgt11 cDNA library to obtain the human sequence and a murine library to obtain the murine sequence. The sequences of several partially overlapping clones were compiled to obtain the full-length h-SmLIM/CRP2 sequence. Both strands of the entire r-SmLIM/CRP2 and h-SmLIM/CRP2 cDNAs were sequenced by the dideoxy chain termination method or on an automated DNA Sequencer (Licor, Lincoln, Nebr.) according to the manufacturer's instructions.

The nucleotide sequences have been submitted to the GENBANK™/EMBL Data Bank with accession numbers U44948 (r-SmLIM/CRP2) and U46006 (h-SmLIM/CRP2).

Cellular Localization of r-SmLIM/CRP2

To construct the expression plasmid Myc-SmLIM/CRP2/pCR3, DNA encoding a c-Myc peptide tag (EQKLISEED; SEQ ID NO:6) was added in frame to the r-SmLIM/CRP2 open reading frame at the N-terminus using PCR techniques. This hybrid DNA fragment was then cloned into the eucaryotic expression vector pCR3 (Invitrogen). COS-7 and 10T1/2 cells were transiently transfected with the Myc-SmLIM/CRP2/pCR3 plasmid using the DEAE-dextran method known in the art. The transfected cells were grown on chamber slides and fixed with 4% paraformaldehyde in PBS. Immunostaining was performed 48 h after transfection with an anti-c-Myc monoclonal antibody (e.g., 9E10; Oncogene) followed by a rhodamine-conjugated goat anti-mouse IgG secondary antibody. Nuclear counterstaining was performed with Hoechst 33258 according to the manufacturer's instructions.

Chromosomal Localization of h-SmLIM/CRP2

The chromosomal location of h-SmLIM/CRP2 was determined using the BIOSMAP Somatic Cell Hybrid blot (BIOS Laboratories, Conn.), which contains DNA from 20 somatic cell hybrid cell lines plus 3 control DNAs (human, hamster, and mouse). A full-length h-SmLIM/CRP2 fragment was randomly primed and hybridized as recommended by the manufacturer. The blot was washed according to the manufacturer's instructions and then exposed to Kodak XAR film at −80° C.

RNA Extraction and RNA Blot Analysis

Total RNA was isolated from cultured cells, rat organs, embryonic stem cells, and mouse embryos by guanidinium isothiocyanate extraction and centrifugation through cesium chloride. The mouse embryo samples (7–10 days old) included placenta and yolk sac tissue. Carotid artery total RNA was obtained by the RNA-Zol method (Cinna/Biotecx Laboratories International, Houston, Tex.) from adult male Sprague-Dawley rats that had been subjected to balloon injury (Zivic-Miller Company, Zelienople, Pa.). Human poly $A^+$ RNA was purchased from Clontech Laboratories (Palo Alto, Inc. Calif.). All RNA was fractionated on a 1.3% formaldehyde-agarose gel and transferred to nitrocellulose filters. The filters were then hybridized with the appropriate $^{32}$P-labeled, random primed cDNA probes using standard methods. The hybridized filters were washed in 30 mM sodium chloride, 3 mM sodium citrate, and 0.1% SDS at 55° C. and autoradiographed on Kodak XAR film at −80° C. To control for differences in RNA loading, the blots were hybridized with an 18S-specific or 28S-specific oligonucleotide probe. The filters were scanned and radioactivity was measured on a PhosphorImager running the ImageQuant software (Molecular Dynamics, Sunnyvale, Calif.).

In vitro Transcription and Translation

The complete r-SmLIM/CRP2 open reading frame was cloned into the eucaryotic expression vector pCR3 (Invitrogen). In vitro transcription and translation was performed in the TNT-coupled wheat germ extract system (Promega, Madison, Wis.) according to the manufacturer's instructions. The transcribed and translated products were resolved on a 10% SDS-PAGE Tricine gel, and autoradiography was performed with Kodak BMR film at room temperature.

In situ hybridization

Rat SmLIM/CRP2 mRNA was hybridized in situ using standard methods. Adult male Sprague-Dawley rats were perfused with 4% paraformaldehyde. Organs were then postfixed with 4% paraformaldehyde, soaked in 30% sucrose until the tissue sank, embedded in optimum cutting temperature (O.C.T.) compound, and stored in isopentane at −80° C. Tissue sections were cut at a thickness of 5 microns. SmLIM/CRP2 mRNA was detected by hybridization with a [$^{35}$S]UTP-labeled antisense cRNA probe synthesized with the SP6 RNA polymerase from HindIII-linearized r-SmLIM/CRP2 in Bluescript II SK+. For control experiments, a [$^{35}$S]UTP-labeled sense cRNA probe was synthesized under the same conditions. RNA probes were degraded to a length of approximately 100–200 nucleotides by partial hydrolysis for 15 min at 60° C. in 80 mM NaHCO$_3$ and 120 mM Na$_2$CO$_3$. After hybridization, the tissue sections were washed under moderately stringent conditions (Lee et al., 1993, Endocrinology 132:2136–2140). The dried tissue sections were then dipped into Kodak NTB2 emulsion (Eastman Kodak, Rochester, N.Y.) and exposed for 2–4 days at 40° C. Counterstaining was performed with hematoxylin-eosin.

Isolation and Characterization of r-SmLIM/CRP2 and h-SmLIM/CRP2 cDNA

The nucleotide sequence of the r-SmLIM/CRP2 cDNA revealed a 582-bp open reading frame encoding a 194 amino-acid protein. Analysis of this frame identified two LIM domains separated by a glycine-rich region and a putative nuclear localization signal.

TABLE 1 shows the complete nucleotide (upper line) and deduced amino acid (lower line) sequences of r-SmLIM/CRP2. Residues composing the two LIM domains are in boldface, a putative nuclear localization signal is underlined, and the polyadenylation signal is underlined and in italics. The nucleotide sequence flanking the putative initiation methionine complied with the Kozak consensus sequence for initiation of translation. A 21 kDa polypeptide was encoded by the r-SmLIM/CRP2 open reading frame.

The entire r-SmLIM/CRP2 cDNA was cloned into the PCRIII eucaryotic expression vector. In vitro transcription and translation (Promega) of this expression plasmid with wheat germ lysate revealed a protein product of 21-kDa (FIG. 1).

Conservation of SmLIM/CRP2 Among Species

To determine whether SmLIM/CRP2 was conserved across species, the human, rat, and mouse homologues were compared. A comparison of the h-SmLIM/CRP2 and r-SmLIM/CRP2 open reading frames revealed 93% identity at the cDNA level and 99% identity at the amino acid level (TABLES 2 AND 3). Comparison of the open reading frames of murine SmLIM/CRP2 (m-SmLIM/CRP2) and r-SmLIM/CRP2 revealed 97% identity at the cDNA level and 100% identity at the amino acid level (TABLE 3). A GENBANK™ search indicated that SmLIM/CRP2 shares homology with the cysteine-rich protein (CRP) family, a characteristic reflected in the name of this novel polypeptide. TABLE 2 compares r-SmLIM/CRP2 and h-SmLIM/CRP2 with their rat and human CRP counterparts and rat MLP. Although an amino acid sequence comparison of r-SmLIM/CRP2 and h-SmLIM/CRP2 shows 99% identity (TABLE 3), a comparison of r-SmLIM/CRP2 with r-CRP shows only 79% identity. These data indicate that SmLIM/CRP2 and CRP are related but different genes.

TABLE 2 shows a sequence alignment of rat (r)-SmLIM/CRP2 and human (h)-SmLIM/CRP2 proteins to the LIM proteins r-CRP, h-CRP, and r-MLP. Consensus sequence indicates residues conserved in all five proteins. Cysteine and histidine residues composing LIM domains are underlined.

TABLE 1

```
  1 ACGAGCTAGACCTCCCTAGCTCCGCCCGCCGCGTGCTCCCGCCTCCCACTCGGAATGCCT
                                                              M  P

61 GTCTGGGGCGGTGGAAATAAGTGCGGGCCTGCGGGAGAACCGTGTACCACGCTGAAGAG
     V  W  G  G  G  N  K  C  G  A  C  G  R  T  V  Y  H  A  E  E

121 GTGCAGTGTGATGGGCGGACGTTCCACCGCTGCTGCTTTCTGTGCATGGTTTGCAGGAAA
     V  Q  C  D  G  R  T  F  H  R  C  C  F  L  C  M  V  C  R  K

181 AATTTAGACAGCACAACAGTGGCAATTCATGATGAAGAGATCTACTGCAAATCATGCTAC
     N  L  D  S  T  T  V  A  I  H  D  E  E  I  Y  C  K  S  C  Y

241 GGAAAGAAGTATGGACCAAAAGGCTATGGTTATGGCCAGGGCGCTGGCACGCTCAACATG
     G  K  K  Y  G  P  K  G  Y  G  Y  G  Q  G  A  G  T  L  N  M

301 GACCGTGGTGAGAGGCTGGGCATCAAGCCAGAGAGTCCTCAACCTCACAGGCCTACAACA
     D  R  G  E  R  L  G  I  K  P  E  S  A  Q  P  H  R  P  T  T

361 AATCCAAACACTTCTAAATTTGCCCAGAAATATGGAGGTGCTGAGAAGTGCTCCAGATGT
     N  P  H  T  S  K  F  A  Q  K  Y  G  G  A  E  K  C  S  R  C

421 GGGGATTCTGTGTATGCTGCTGAGAAGATCATTGGAGCTGGAAAGCCCTGGCACAAAAAC
     G  D  S  V  Y  A  A  E  K  I  I  G  A  G  K  P  W  H  K  N

481 TGTTTCCGATGTGCCAAGTGTGGGAAGAGTCTGGAGTCTACAACTCTGACTGAGAAGGAA
     C  F  R  C  A  K  C  G  K  S  L  E  S  T  T  L  T  E  K  E
```

TABLE 1-continued

```
541 GGTGAAATCTACTGTAAAGGGTGCTACGCAAAGAACTTTGGGCCCAAGGGATTCGGCTAT
     G   E   I   Y   C   K   G   C   Y   A   K   N   F   G   P   K   G   F   G   Y

601 GGTCAAGGAGCAGGGGCCCTTGTTCATGCTCAGTAGTGGTGTAAACCCAGTAAGCATGGC
     G   Q   G   A   G   A   L   V   H   A   Q        (SEQ ID NO: 8)

661 AAAGAACCTCCATTAATGTGGATGGCCTTACCGCACTCAGGCTGTGCATCGGCCAGCACT

721 CAGCACTGTGTAGCACACACGCTATGTGCACAATCGGGCTGGACAGGAAGCACTACACTC

781 TCCTGCCCATCCGCTAACGTTTAAGAACGTTCTTTTACATTTGGAATAAAATTTTGGTTT

841 GATTTGAAAAAAAAAAAAAAAAAAAAAAAAAAAAAAAAAAA (SEQ ID NO: 7)
```

TABLE 2

```
             1         .         .         .         .         50
  r-SmLIM    MPVWGGGNKCGACGRTVYHAEEVQCDGPTFHRCCFLCMVCRKNLDSTTVA
  h-SmLIM    MPVWGGGNKCGACGRTVYHAEEVQCDGRSFHRCCFLCMVCRKNLDSTTVA
    r-CRP    MPNWGGGKKCGVCQKTVYFAEEVQCEGNSFHKSCFLCMVCKKNLDSTTVA
    h-CRP    MPNWGGGKKCGVCQKTVYFAEEVQCEGNSFHKSCFLCMVCKKNLDSTTVA
    r-MLF    MPNWGGGKKCGVCQKTVYFAEEIQCNGRSFHKTCFHCMACRKALDSTTVA
Consensus    MPNWGGGNKCGNCNNTVYNAEEVQCNGNNFHNNCFNCMNCNKNLDSTTVA 51         .         .         .         .        100
  r-SmLIM    IHDEEIYCKSCYGKKYGPKGYGYGQGAGTLNMDRGERLGIKPESAQPH R
  h-SmLIM    IHDEEIYCKSCYGKKYGPKGYGYGQGAGTLNMDRGERLGIKPESVQPH R
    r-CRP    VHGEEIYCKSCYGKKYGPKGYGYGQGAGTLSMDKGESLGIKHEEAPGH R
    h-CRP    VHGEEIYCKSCYGKKYGPKGYGYGQGAGTLSTDKGESLGIKHEEAPGH R
    r-MLF    AHESEIYCKVCYGKKYGPKGIGFGQGAGCLSTDTGEHLGLQFQQSPKPAE
Consensus    NHNNEIYCKNCYGNKYGPKGNGYGQGAGNLNNDNGENLGNNNNNNNNNR 101         .         .         .         .        150
  r-SmLIM    PTTNPNTSKFAQKYGGAEKCSRCGDSVYAAEKIIGAGKPWHKNCFRCAKC
  h-SrnL     PTTNPNTSKFAQKYGGAEKCSRCGDSVYAAEKIIGAGKPWHKNCFRCAKC
    r-CRP    PTTNPNASKFAQKIGGSERCPRCSQAVYAAEKVIGAGKSWHKSCFRCAKC
    h-CRP    PTTNPNASKFAQKIGGSERCPRCSQAVYAAEKVIGAGKSWHKACFRCAKC
Consensus    NNTNNNNSKFNNKNGNNENCNRCNNNVYAAEKNNGNGKNWHKNCFNCANC 151         .         .         .       194
  r-SmLIM    GKSLESTTLTEKEGEIYCKGCYAKNFGPKGFGYGQGAGALVHAQ (SEQ ID NO:8)
  h-SmLIM    GKSLESTTLTEKEGEIYCKGCYAKNFGPKGFGYGQGAGALVHAQ (SEQ ID NO:1)
    r-CRP    GKSLESTTLADKDGEIYCKGCYAKNFGPKGFGFGQGAGALVHSE (SEQ ID NO:9)
    h-CRP    GKSLESTTLADKDGEIYCKGCYAKNFGPKGFGFGQGAGALVHSE (SEQ ID NO:10)
    R-CRP    GKSLESTNVTDKDGELYCKVCYAKNFGPTGIGFGGLTHQVEKKE (SEQ ID NO:11)
Consensus    GKNLESTNNNNKNGENYe,uns CKNCYAKMFGPNGNGNGNNNNNNNNNN (SEQ ID
             NO:12)
```

TABLE 3

| | | Nucleotides (%) | Amino Acids (%) |
|---|---|---|---|
| r-SmLIM/CRP2 vs. | m-SmLIM/CRP2 | 97 | 100 |
| | h-SmLIM/CRP2 | 93 | 99 |
| | r-CRP | 73 | 79 |
| | h-CRP | 72 | 79 |
| | r-MLP | 65 | 65 |

TABLE 4

```
  1 ATGCCTGTCT GGGGAGGTGG AAACAAGTGT GGGGCCTGTG GAGGACCGT(SEQ ID NO:2)

51 GTACCACGCA AGAGAGGTGC AGTGTGATGG CAGGAGCTTC CACCGCTGCT

101 GCTTTCTCTG CATGGTTTGC AGGAAAAATT TAGATAGCAC AACAGTGGCA

151 ATTCACGATG AAGAGATCTA CTGCAAATCC TGCTACGGAA AGAAGTATGG

201 GCCAAAAGGC TACGGTTATG GCCAGGGCGC TGGCACGCTt aacatggacc 251 gtggcgagag gctgggcatc aaaccagaga gtgttcagcc tcacaggcct
```

TABLE 4-continued

```
301 acaacaaatc caaacacttc taaatttgct cagaaatatg gaggtgctga 351 gaAGTGTTCC AGATGTGGGG ATTCTGTATA TGCTGCCGAG AAGATAATTG

401 GAGCTGGAAA GCCCTGGCAC AAAAACTGTT TCCGATGTGC AAAGTGTGGG

451 AAGAGTCTTG AATCAACAAC TCTGACTGAA AAAGAAGGTG AAATCTATTG

501 TAAAGGATGC TATGCAAAGA ACTTTGGGCC CAAGGGATTT GGCTATGGCC

551 AAGGAGCAGG GGCTCTTGTT CATGCCCAGT AAGATGTAAA CCCTGAACTA

601 AACATCACAC ACTGAGAATC TCTTCATAAT CTAGGCACAG ATAATCTTTA

651 ACCCGGAATT CCGCCGATAC TGACGGGCTC CAGGAGTCGT CGCCACCAAG

701 CCGAATTCCA GCACACTGGC GGcCGTTACT AGTGGATCCG A
```

TABLE 3 shows the percentage nucleotide and amino acid identity of r-SmLIM versus mouse m-SmLIM and h-SmLIM homologues, r-CRP, h-CRP, and r-MLP.

TABLE 4 shows the nucleotide sequence of the h-SmLIM cDNA

TABLE 5 shows the nucleotide sequence of m-SmLIM/CRP2 cDNA and amino acid sequence of the m-SmLIM/CRP2 polypeptide.

TABLE 5

```
    AGTCTCCGGATCCGCCCGCGGCTTTCCTCGGTCAGACCTCGTTAGCTCCGCCCGCCGCGT  60  (SEQ ID NO:13)

GCTCCCTCCTCCCACTCGGAATGCCTGTCTGGGCGGTGGAAATAAGTGCGGGGCCTGCG  120
1                    M  P  V  W  G  G  G  N  K  C  G  A  C  G

GGAGAACCGTGTACCACGCGGAAGAGGTGCAGTGCGATGGGCGGACGTTCCATCGCTGCT  180
15   R  T  V  Y  H  A  E  E  V  Q  C  D  G  R  T  F  H  R  C  C

GCTTCCTGTGCATGGTTTGCAGGAAAAATTTAGACAGCACAACAGTGGCGATTCATGATG  240
35   F  L  C  M  V  C  R  K  N  L  D  S  T  T  V  A  I  H  D  E

AAGAGATCTACTGCAAATCCTGCTACGGAAAGAAGTATGGACCAAAAGGCTATGGTTATG  300
55   E  I  Y  C  K  S  C  Y  G  K  K  Y  G  P  K  G  Y  G  Y  G

GCCAGGGCGCTGGCACGCTCAACATGGACCGCGGTGAGAGACTGGGCATCAAGCCAGAGA  360
75   Q  G  A  G  T  L  N  M  D  R  G  E  R  L  G  I  K  P  E  S

GTGCTCAACCTCACAGGCCTACGACAAATCCAAACACTTCTAAATTTGCCCAGAAATATG  420
95   A  Q  P  H  R  P  T  T  N  P  N  T  S  K  F  A  Q  K  Y  G

GAGGAGCTGAGAAGTGTTCCAGGTGTGGGGATTCCGTGTATGCTGCGGAGAAGATCATTG  480
115  G  A  E  K  C  S  R  C  G  D  S  V  Y  A  A  E  K  I  I  G

GAGCTGGGAAGCCCTGGCACAAAAAACTGTTTCCGGTGTGCCAAGTGTGGGAAGAGTCTGG  540
135  A  G  K  P  W  H  K  N  C  F  R  C  A  K  C  G  K  S  L  E

AGTCTACAACTCTGACTGAGAAAGAAGGCGAAATCTACTGTAAAGGGTGCTACGCAAAGA  600
155  S  T  T  L  T  E  K  E  G  E  I  Y  C  K  G  C  Y  A  K  N

ACTTTGGGCCCAAGGGATTTGGCTATGGTCAAGGGGCAGGGGCCCTTGTTCATGCTCAGT  660
175  F  G  P  K  G  F  G  Y  G  Q  G  A  G  A  L  V  H  A  Q  *

AATGGTGTGAACCAGTAAGCACGACAGAGAATCTCCATTACCAAACTGCAGATGGCGTTT  720  (SEQ ID NO:14)

ATGGCGCTCACTACTGTGAAACAGCCAGCACTTGGCACTGGGCATCACCGAGCTGCCTGT  780

GGGGGCTGGACCGACAGCGCTGCACTCTCCCGCCCACTCACTAGCGTCTAAGAGCATTCT  840
```

The number of nucleotide and amino acid sequence positions are indicated in the right and left margins, respectively. The potential nuclear localization signal is underlined. The conserved cysteine and histidine residues of the two LIM domains are in bold, and the adjacent glycine residues in the glycine-rich repeat are in italics.

Identification of the Transcription Start Site and Potential cis-acting Sequences The transcription start site was determined using an end-labeled SmLIM/CRP2 fragment in an S1 nuclease protection assay. Protected fragments were observed when the probe was incubated with total RNA prepared from primary culture of mouse aortic smooth muscle cells but not when the probe was incubated with tRNA or total RNA from mouse skeletal muscle. The transcription start site was determined to be 80 bp 5' of the translation initiation codon and it corresponds to an A nucleotide, consistent with the result obtained from 5'-RACE. The 5'CA3, nucleotide pair at this site is the most common type of eukaryotic transcription start site. The transcription start site included a pyrimidine-rich sequence that is homologous but not identical to a consensus initiator repeat sequence (YAYTCYYY; SEQ ID NO:41) in that a G residue replaces the Y at +2 position. The 5'-flanking region of SmLIM/CRP2 was characterized by islands rich in G and C (FIG. 9). A TATA-like sequence (TTTAAA; SEQ ID NO:42) was located 27 bp 5' of the transcription start site. A consensus CCAAT (SEQ ID NO:43) box was not found near the transcription start site. Comparison of the 5'-flanking sequence with sequences in the Transcription Factors Data Base revealed a series of five Sp1 sites located between nucleotides −308 and −39, and two additional Sp1 sites located within the untranslated region of the first exon. One E-box/bHLH transcription factor binding site (CANNTG; SEQ ID NO:44) was located at position −334, one NFκB-binding element (GGGRNTYYC; SEQ ID NO:45) at −305, and one C/EBP binding site at bp −230. In addition, two consensus AP2 sites were found within the first exon. Finally, four CACCC (SEQ ID NO:46)-boxes were located at bp −349, −312, −87, and +78.

Analysis of the Promoter Activity of the 5'-flanking Sequence of SmLIM/CRP2

Figure 10:
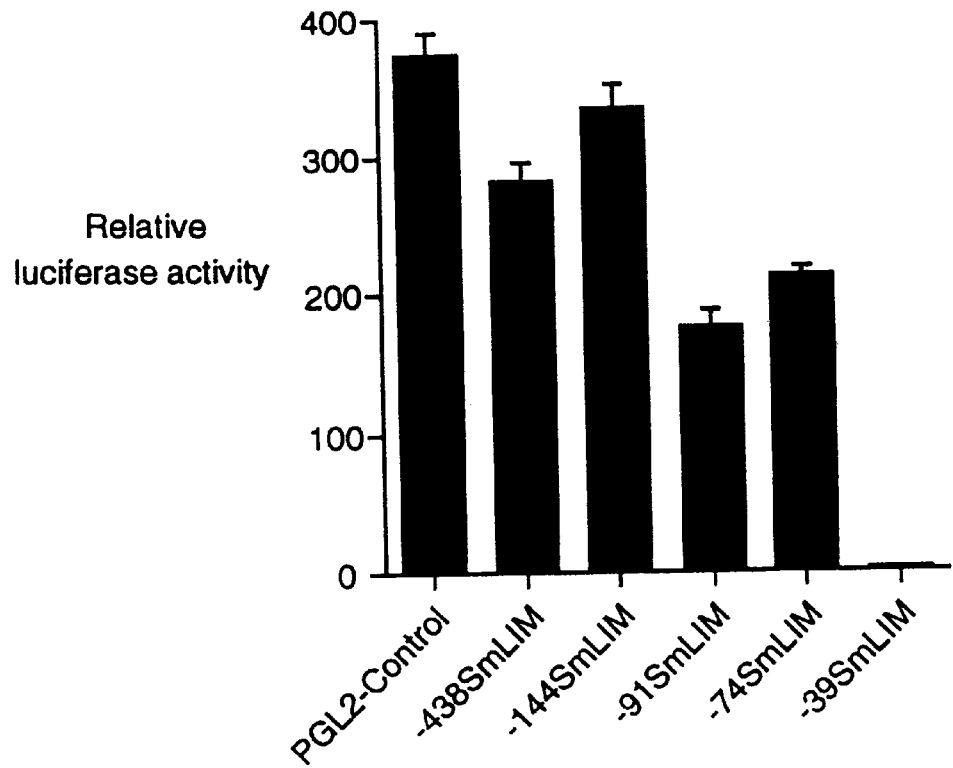
FIG. 10 is a bar graph showing the results of a functional analysis of the mouse SmLIM/CRP2 promoter. Luciferase promoter constructs containing various lengths of SmLIM/CRP2 5' flanking sequence were transfected in rat smooth muscle cells. All constructs were cotransfected with the control plasmid pOPRSVICAT to correct for transfection efficiency, and luciferase activity was expressed relative to the activity of −39SmLIM/CRP2 (mean±SEM).
Figure 11:
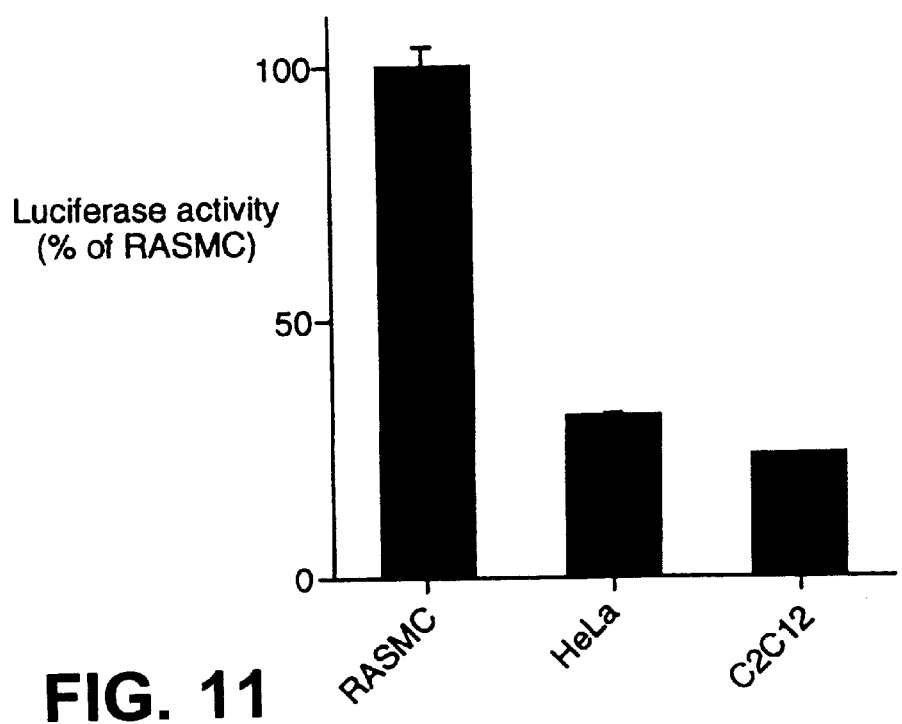
FIG. 11 is a bar graph showing SmLIM/CRP2 promoter activity in different cell types. The luciferase reporter construct −438SmLIM/CRP2 was transfected into various cell types, and luciferase activity measured. Transfection efficiency was corrected by cotransfection with pOPRSVICAT for RASMC, and pSVβgal for HeLa and C2C12 cells. Promoter activity was normalized for transfection efficiency in different cell types by comparing the activity in each cell type to to the activity observed in that cell type transfected with pGL2-Control plasmid. Luciferase activity was expressed as the percentage of promoter activity in detected in RASMC. The results represent the average of three transfection experiments.

To determine whether the sequence flanking the 5' end of the SmLIM/CRP2 gene has promoter activity, the plasmid −438SmLIM/CRP2 (which contains 438 bp of the mouse SmLIM/CRP2 5'-flanking region linked to the luciferase gene) was transfected into PASMC. The control plasmid, pGL2-Control, was also transfected into RASMC. The luciferase activity generated by −438SmLIM/CRP2 was 75% that of pGL2-Control. These data indicate that the 5'-flanking region of the SmLIM/CRP2 coding sequence contains potent promoter activity. To further localize the cis-acting elements, reporter plasmids containing various lengths of SmLIM/CRP2 5'-flanking region were into RASMC (FIG. 10). As little as 74 bp of SmLIM/CRP2 promoter directed high level of promoter activity; however, a further deletion of 35 bp of promoter sequence markedly decreased the luciferase activity. These data indicate that basepairs −39 to −74 of the SmLIM/CRP2 gene contain most of the promoter activity. To determine whether the SmLIM/CRP2 promoter was active in other cell types, −438 SmLIM/CRP2 was also transfected into HeLa cells and C2C12 myoblasts. The −438SmLIM/CRP2 conferred 3- to 4-fold higher activity in RASMC than HeLa and C2C12 cells (FIG. 11).

TABLE 6 and 7 show the m-SmLIM/CRP2 promoter. In TABLE 6, the transcription start site is indicated with an arrow.

TABLE 6

```
  1 TGAGGAATGC AGCTCTTtCG CGACAGGAAA GCTGCGGATT CCAGAAGCCG(SEQ ID NO:16)

51 GGATTCTGAC CAGAGACTAT CTGCACCGGG GAGTCCTGCA CCCCGAGCTA

101 ACATATGgCG TTTGTGCAGT AAAAGGGTGG CGGGAATCCC ACGGGCGAC

151 ACCGGATCTC GCTGGCTCCG GGCCGATCCT GAGTGCTCCG GACGTCCCGG

201 GACCGCGGGT AGGAGCAGCC GAGACGTGGG AGACTCGGAC GCGGGAAGCC

251 GCAGGAAGAG GCGGATTCCG GTCTTTTTGT CTCGGGGCCA GAGCaCGAAA

301 CCCGCAtCGG ATCCCCGAGC TCACGCCGGG CGGAGACCAT CGCACACCCG

351 AGGGGCATGA CCGATGGCTG AGTCGGAACA AGCCACGCCC AACATAAGTC

→
401 TTTAAAAGCG GGCACACGCG TCCCGCCAGT CTCCGGATCC GCCCGCCGGC

451 TTTCCTCGGT CAGACCTCGT TAGCTCCGCC CGCCGCGTGC TCCCTCCTCC

501 CACTCGGgtg agtcctaggc tc
```

TABLE 7

```
  1 TGAGGAATGC AGCTCTTtCG CGACAGGAAA GCTGCGGATT CCAGAAGCCG(SEQ ID NO:3)

51 GGATTCTGAC CAGAGACTAT CTGCACCGGG GAGTCCTGCA CCCCGAGCTA

101 ACATATGgCG TTTGTGCAGT AAAAGGGTGG CGGGAATCCC ACGGGCGAC

151 ACCGGATCTC GCTGGCTCCG GGCCGATCCT GAGTGCTCCG GACGTCCCGG

201 GACCGCGGGT AGGAGCAGCC GAGACGTGGG AGACTCGGAC GCGGGAAGCC

251 GCAGGAAGAG GCGGATTCCG GTCTTTTTGT CTCGGGGCCA GAGCaCGAAA

301 CCCGCAtCGG ATCCCCGAGC TCACGCCGGG CGGAGACCAT CGCACACCCG

351 AGGGGCATGA CCGATGGCTG AGTCGGAACA AGCCACGCCC AACATAAGTC

401 TTTAAAAGCG GGCACACGCG TCCCGCC
```

Sp1 Protein Binding to the Core Promoter of SmLIM/CRP2

Using the DNA fragment encoding bp −39 to −74 (which contains two Sp1 sites) as a probe in gel-mobility-shift analysis, a specific DNA-protein complex was detected when the probe was incubated with nuclear extracts prepared from RASMC. The DNA-protein complex was deemed to be specific because a 100-fold molar excess of unlabeled identical competitor, but not a DNA fragment encoding the ATF sequence, abolished the binding complex. In addition, this DNA-protein complex was competed away by a DNA fragment containing consensus Sp1 oligonucleotide, indicating the presence of Sp1 binding proteins in the complex. To further characterize the binding proteins, gel mobility shift assay was performed in conjunction with antibodies. Antibodies to Sp1 supershifted the upper part of the DNA-protein complex. In contrast, antibodies to AP2 had no effect. These results suggest the presence of Sp1 proteins in the upper DNA-protein complex. The lower part of the complex may contain other members of the Sp family.

Genomic Organization of the m-SmLIM/CRP2 Gene

Using the SmLIM/CRP2 full length cDNA as a probe to screen a library prepared from mouse genomic DNA (129SvJ), several overlapping clones encoding SmLIM/CRP2 genomic sequence were isolated. The mouse SmLIM/CRP2 gene was found to be organized into six exons and five introns spanning approximately 20 kb (FIG. 8). All exon/intron boundaries were determined by DNA sequencing, and intron sizes were determined by PCR using oligos derived from flanking exons. All assigned exon/intron boundaries are in agreement with consensus 5'-GT and 3'-AG splicing sequences. The average length of the m-SmLIM/CRP2 exons, 145 bp, is consistent with the length of exons in general, i.e., 137 bp. Exon 1 contains the 5'-untranslated region. Exon 2 contains the entire 5' finger and the first cysteine of the 3' finger of the first LIM domain. Exon 3 contains the rest of 3' finger and the putative nuclear localization signal. Exon 4 encodes the first two cysteines of the 5' finger of the second LIM domain and exon 5 contains the rest of the 5' finger and most of the 3' finger except the last cysteine. Exon 6 contains the rest of the coding region and 3' untranslated region. At the 3' end of the m-SmLIM/CRP2 gene, exon 6 contains a consensus polyadenylation signal AATAAA motif. Poly(A) addition occurs 11 bp downstream from this motif.

TABLE 8 shows the m-SmLIM/CRP2 genomic sequence.

TABLE 8

SmLIM-Genomic Sequence

```
EXON 1 AGTCTCCGGATCCGCCCGCGGCTTTCCTCCGTCAGACCTCGTTAGCTCCGCC
       CGCCGCGTGCTCCCTCCTCCCACTCGG (SEQ ID NO:19)

gtgagtcctaggctc...........gagctctgtgagtaagagcgatgtttcctccacgatatgc
       tagataaaaatctgggggtgggggtaaccagaagagggacaaagcaccttgtactaattgtttaa
       atatttaataaaggtctcatcaggaaacctaatagaggtctgcaccatttaatggttgtatgggaa
       tcacgcctttaaggcaaagatgagctttctctgctacagacta..........aagcatctgctag
       tacgcactgtctcgtggctgaagcagccggagggaactcgtaaaacaacgcatcctaatgcatcct
       ttgttccgcag (SEQ ID NOS:20,21,22)

EXON 2 CATGCCTGTCTGGGGCGGTGGAAATAAGTGCGGGGCCTGCGGGAGAACCGTGTACCACGCGGAAGA
        M   P   V   W   G   G   G   N   K   C   G   A   C   G   R   T   V   Y   H   A   E   E
       GGTGCAGTGCGATGGGCGGACGTTCCATCGCTGCTGCTTCCTGTGCA (SEQ ID NO:23)
        V   Q   C   D   G   R   T   F   H   R   C   C   F   L   C   M (SEQ ID NO:24)
       gtgagtatggtcccctcccccttcagttcacctctggaagaaaaataacaatgctagctaagagaa
       atggtttagagtgacggggttttttgtttgtttgtttttgttttaaccgctgagtcatctcccta
       gcccaatgcggtgttttatgtcattgatcttaagacgctgaggactgagccagagggaagaccacc
       tagccctcagttctggccagttggcttagcctttgtcacctctgtctgtgtcctcggg........
       ......gtcatttggaggcacctctgtttttaagttaaagctatatatatatatatatatatatata
       tatatatatatatatatatatattcatattttaatgatgtttaaaatctatctaccctggggct
       tag (SEQ ID NOS:25,26)

EXON 3 TGGTTTGCAGGAAAAATTTAGACAGCACAACAGTGGCGATTCATGATGAAGAGATCTACTGCAAAT
          V   C   R   K   N   L   D   S   T   T   V   A   I   H   D   E   E   I   Y   C   K   S
       CCTGCTACGGAAAGAAGTATGGACCAAAAGGCTATGGTTATGGCCAGGGCGCTGGCACGCTCAACA
        C   Y   G   K   K   Y   G   P   K   G   Y   G   Y   G   Q   G   A   G   T   L   N   M
       TGGACCGCGGTGAGAGACTGGGCATCAAGCCAGAGAG (SEQ ID NO:27)
          D   R   G   E   R   L   G   I   K   P   E   S (SEQ ID NO:28)
       gtgagagaatgttaccctcttaaaagcgggtagaacagctcctgtcgctcaggcaccaggagcctg
       catatttagtttaaactaagcaagcaaaataaaatgtgacctctactaaatactcatatgattact
       acgacgttctgtaacgtcataatattgacagttttgtatctaaaaatcttagtaatgaatgcaggg
       acttctagccctggttatatagcattttaactgatatcaggaaaacataaatctcaaggaactgac
       ttacttaatatcccatacgcactggagatcaaatatcttgaaatgagtgtttgaattctgagatcg
       ttctcatatgattaactgtccacggaaagtccttagtcactctttcctcaggaaattacatccttc
       aacttagaaattaaaaccatttcctcgttctgatgatttgagggacaaatcg............aa
       atgtttcacaatatacattacctctaaatcttcccatcaatgaaaactaaattcacaagacccca
       agcaataagcaagctctgtgtgcacgccctatgtgcagtggtaaccctgtctgtcccttccagccg
       ggccctggtctggtcttcctctgcgatcaggtctaaggaattcctcctcccagaggtcttcttag
       gactcaaaaccatggcctgccttttaacacacagattaaa..........cgaagctcctgttagc
       tcaggaggaacatttggagaaacactgcctcattttttttctccgttcccccag (SEQ ID NOS:29,30,31)

EXON 4 TGCTCAACCTCACAGGCCTACGACAAATCCAAACACTTCTAAATTTGCCCAGAAATATGGAGGAGC
        A   Q   P   H   R   P   T   T   N   P   N   T   P   K   F   A   Q   K   Y   G   G   A
       TGAGAAGTGTTCCAGGTGTGGGGATTCCTGTATGCTGCGGACAAGATCATTGGAGCTGGGAAG (SEQ ID
       NO:32)
        E   K   C   S   R   C   G   D   S   V   Y   A   A   E   K   I   I   G   A   G   K(SEQ ID:33)
       gtagggcgctgtctctaagtggtaactgcagcacacactcacacacacacagggtgctgtctgtct
```

TABLE 8-continued

SmLIM-Genomic Sequence

```
      ctaactggtaactgtaataaacacacacatacatacacaagcatacatagacacacacacacac
      acacacatac...........ctgctcccagcaaacagcccttactggtggctagaagatatgac
      agcaaagaggccagctttctagctgagccaaaccgtagcctgaggaggctgcttgtgcgctggttt
      tcccagccacttgctgcatctagatcgagccaaaggaaacaagcctctcaatgtcctaactcagct
      gtctcttccag (SEQ ID NOS:34,35)

EXON 5 CCCTGGCACAAAAACTGTTTCCGGTGTGCCAAGTGTGGGAAGAGTCTGGAGTCTACAACTCTGACT
       P  W  H  K  N  C  F  R  C  A  K  C  G  K  S  L  E  S  T  T  L  T
       GAGAAAGAAGGCGAAATCTACTGTAAAG (SEQ ID NO:36)
       E  K  E  G  E  I  Y  C  K  G (SEQ ID NO:37)
      gtaaaaactcggttctgctgtctgttagtgtcaccagaaagggagacatcgtgcactgttacctt
      tgaaaatgagaccgacatcttaggacagtgattacttcttccattcctactgtgtgtgttaagtcc
      acacggctgggggatctggccgaatggtaaaagcttgcctatgtagcacattcacaaggaggccacg
      ctcagcacggcctcccaacctctgacttcctactttaagccaagcatatgactacgtgagggtga
      cacacagaaggcagctggatttcagcctgcagctcatcacaatcctaacttggatgccgtgggaat
      tcctggactcgcttcaaacaaggatgctcatagcagagcccattttatatcttaaactgacctctg
      cagagcctccagttggcttttaaattaatggccatttgttagtgacctctgattaactctcccttt
      cctttgtag (SEQ ID NO:38)

EXON 6 GGTGCTACGCAAAGAACTTTGGGCCCAAGGGATTTGGCTATGGTCAAGGGGCAGGGGCCCTTGTTC
          C  Y  A  K  N  F  G  F  K  G  F  G  Y  G  Q-
          G  A  G  A  L  V  H
       ATGCTCAGTAATGGTGTGAACCAGTAAGCACGACAGAGAATCTCCATTACCAAACTGCAGATGGCG
          A  Q  *  (SEQ ID NO:40)
       TTTATGGCGCTCACTACTGTGAAACAGCCAGCACTTGGCACTGGGCATCACCGAGCTGCCTGTGGG
       GGCTGGACCGACAGCGCTGCACTCTCCCGCCCACTCACTAGCGTCTAAGAGCATTCTTTTACATTT
       GAAATAAAATTTTGGCTTG (SEQ ID NO:39)
      atttgggtaccacctcttaattaaccttttcagaggagctgttgtgattttttagatgatgagaagtt
      atctggttccttcctccagtgaaaaccagtctcctgattaaaaaaaaaaaaaaagaccgtttcttta
      aaaagacaatcaattcctttatgcagtaggctaacatttgcactctgagagctgaaaacgacattt
      tactttttgagattttcattcatatatatatatatatacatatatatatatatatatatatatat
      atatatatatatatacaaaacactccgtgga (SEQ ID NO: 17)
```

SmLIM/CRP2 is a highly conserved, two-LIM-domain nuclear protein of the LIM-only class. Other members of this class include RBTN2, MLP, and CRP. Like SmLIM/CRP2, RBTN2 and MLP are nuclear proteins with two LIM-domains, and they are highly conserved across species (Arber et al. 1994, Cell 79:221–231; Warren et al., 1994, Cell 78:45–57). CRP proteins also have two LIM-domains and show high cross-species conservation (Wang et al. 1992, J. Biol. Chem. 267:9176–9184; Weiskirchen et al., 1995, J. Biol. Chem. 270:28946–28954). Sequence comparisons of SmLIM/CRP2 and CRP suggest that the two gene families are related yet distinct (TABLES 2 and 3). In contrast with SmLIM/CRP2, which is a nuclear protein (FIGS. 2A and 2B), CRP has been localized to the cytoskeletal adhesion plaques (Crawford et al., 1994, J. Cell Biol. 124:117–127; Sadler et al., J. Cell Biol. 119:1573–1587). Moreover, h-SmLIM/CRP2 localizes to chromosome 3 (FIG. 3), whereas h-CRP localizes to chromosome 1 (Wang et al., 1992, Genomics 14:391–397). Finally, Northern analysis of r-CRP tissue distribution showed that the size of its mRNA and pattern of expression were distinct from those of r-SmLIM/CRP2. Taken together, these data indicate that SmLIM/CRP2 and CRP are distinct LIM proteins.

Cellular and Chromosomal Localization of SmLIM/CRP2

Figure 2A:
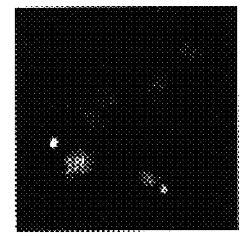
FIG. 2A is a photomicrograph of labeled cells. Cells immunostained with an anti-c-Myc antibody were counterstained with Hoechst 33258 to label the nuclei. Magnification, 600×.
Figure 2B:
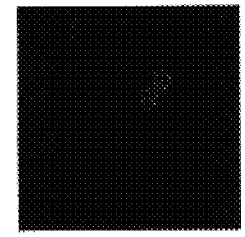
FIG. 2B is a photomicrograph of labeled cells showing the cellular localization of r-SmLIM/CRP2. COS cells were transiently transfected with the c-myc-r-SmLIM/CRP2 hybrid construct or vector alone. Protein expression was assayed 48 h after transfection with an anti-c-myc monoclonal antibody (9E10) followed by rhodamine-conjugated secondary antibody. Magnification, 600×.
Figure 3:
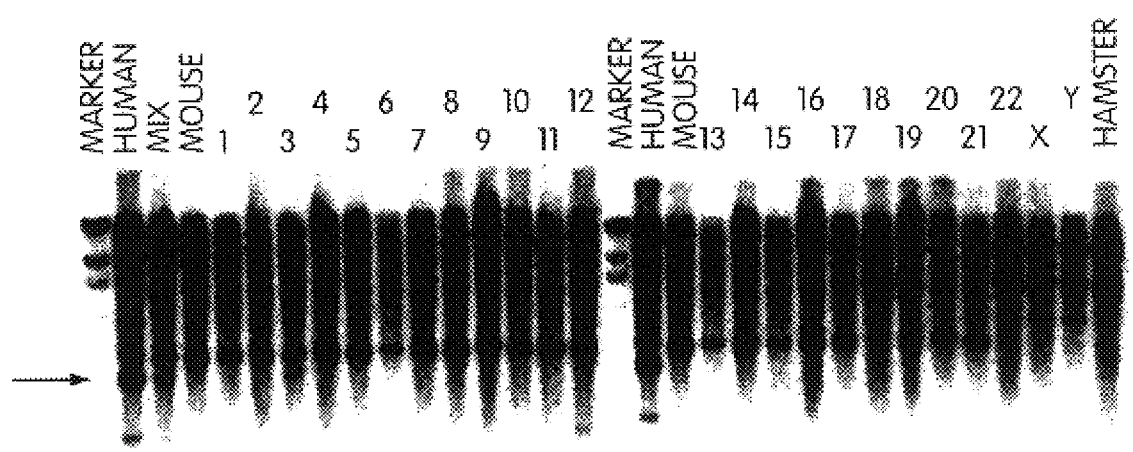
FIG. 3 is a photograph of a Southern blot assay showing chromosomal localization of human (h)-SmLIM/CRP2. Individual chromosomes are numbered 1–22, X, and Y. The three control DNA samples (human, mouse, and hamster) were provided by the manufacturer of the kit (BIOS Somatic Cell Hybrid Blot). Arrow indicates specific signal for h-SmLIM/CRP2 visible only in the human, mix, and chromosome 3 lanes.

The r-SmLIM/CRP2 deduced amino acid sequence contains the putative nuclear localization signal KKYGPK (SEQ ID NO:15), suggesting that SmLIM/CRP2 is a nuclear protein. To determine the cellular localization of SmLIM/CRP2, a plasmid expressing a fusion protein of the c-myc tag and r-SmLIM/CRP2 was made. This plasmid and the control vector alone were transfected into COS cells. The cells were immunostained with an anti-c-myc antibody. Detection of the immunofluorescent signal in the nuclei of COS cells transfected with the c-myc-r-SmLIM/CRP2 fusion plasmid but not the control vector alone indicated that the SmLIM/CRP2 protein localized to the nucleus (FIGS. 2A and 2B). The same experiment was performed with 10T1/2 fibroblasts. SmLIM/CRP2 localized to the nucleus in these cells as well. The chromosomal location of h-SmLIM/CRP2 was mapped with the BIOS Somatic Cell Hybrid Blot. h-SmLIM/CRP2 was found to localize to chromosome 3 (FIG. 3, arrow).

Tissue Distribution of r-SmLIM/CRP2 and h-SmLIM/CRP2

Figure 4A:
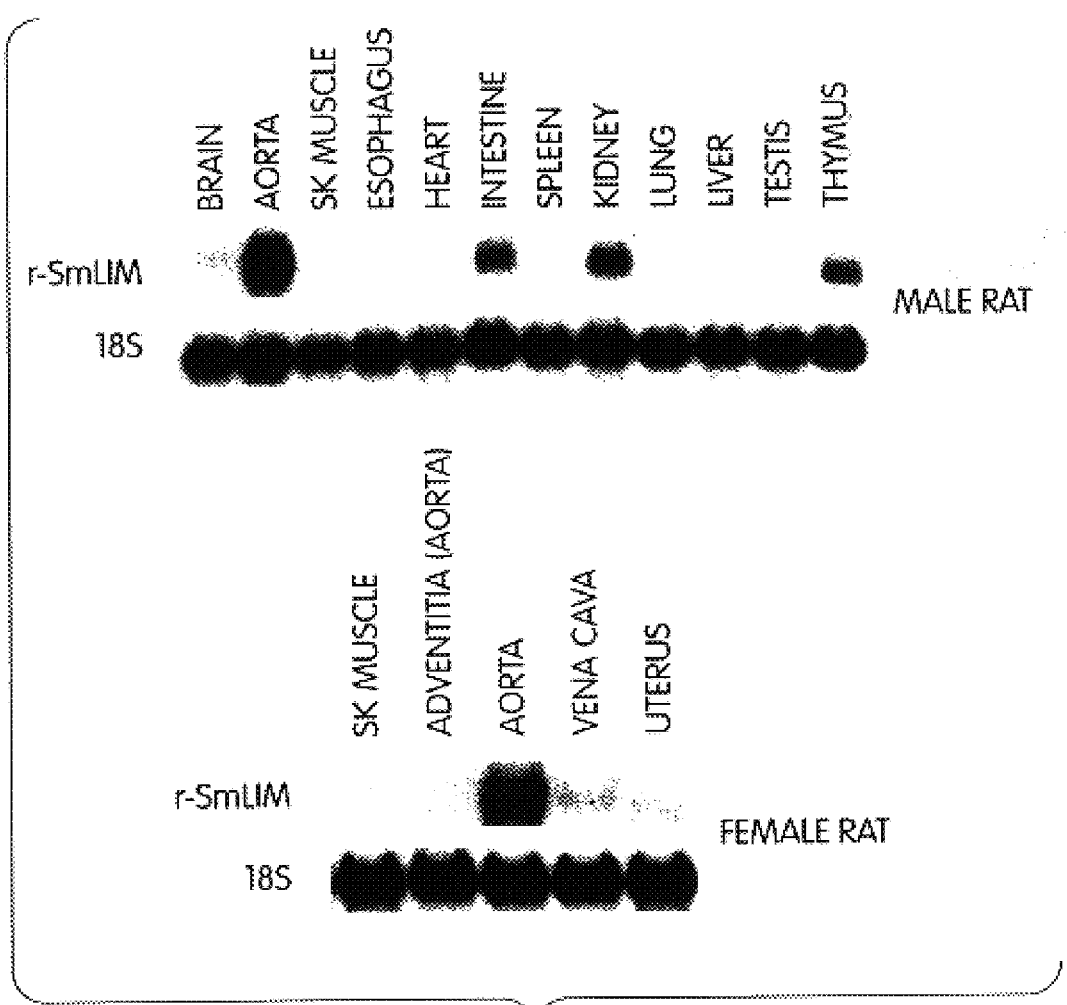
FIG. 4A is a photograph of a Northern blot assay showing r-SmLIM/CRP2 mRNA expression in male and female rat tissues. Northern analysis was performed with 10 µg of total RNA per lane. After electrophoresis, RNA was transferred to nitrocellulose filters and hybridized with a $^{32}$P-labeled r-SmLIM/CRP2 probe. A single r-SmLIM/CRP2 transcript is visible at 1.0 kb. Filters were hybridized with an 18S-specific probe to verify equivalent loading.
Figure 4B:
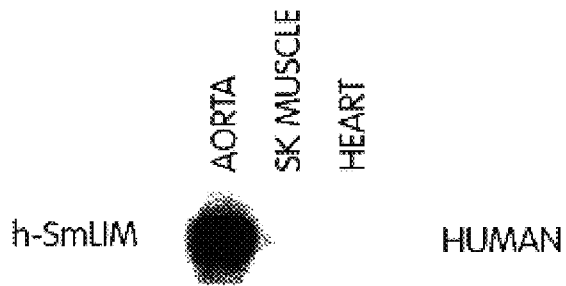
FIG. 4B is a photograph of a Northern blot assay showing h-SmLIM/CRP2 mRNA expression. Northern analysis was performed with 2 µg of poly A+ RNA (Clontech). A 2.1-kb transcript is shown.

Total RNA were isolated from 15 types of tissue from adult male and female rats and analyzed for SmLIM/CRP2 expression by Northern blot analysis (FIG. 4A). A single, intense, 1.0-kb band was detected in the aorta. A much weaker signal was detected in the kidney, thymus, and intestine. SmLIM/CRP2 expression was not detectable in heart and skeletal muscle and was barely detectable in brain, testis, esophagus, lung, liver, aortic adventitia, vena cava, and uterus. These data indicate that r-SmLIM/CRP2 is expressed in tissue containing smooth rather than striated muscle. Expression of SmLIM/CRP2 was found to be much greater in aortic tissue compared to intestinal or uterine tissue, indicating that SmLIM/CRP2 is expressed preferentially in vascular smooth muscle cells. Even among vascular RNAs, r-SmLIM/CRP2 expression was greater in arterial tissue (aorta) compared to venous tissue (vena cava). Consistent with the r-SmLIM/CRP2 expression pattern, h-SmLIM/CRP2 was expressed to a high degree in aorta but not in heart or skeletal muscle (FIG. 4B). The pattern of preferential expression in arterial but not venous smooth muscle cells suggests that smooth muscle cells may be fundamentally different in the two tissue types.

Although SmLIM/CRP2 is highly expressed in smooth muscle cells, it is not expressed in striated muscle cells (FIGS. 4A and 4B). This pattern is in contrast with that of MLP, which is expressed only in the heart and skeletal muscle. When a full-length MLP probe was hybridized to total RNA from aorta and cultured vascular smooth muscle cells, no message was detected. Thus, the expression of the two LIM proteins is distinct within the myogenic cell lineage.

Tissue Distribution of r-SmLIM/CRP2 (In Situ Hybridization)

Figure 5A:
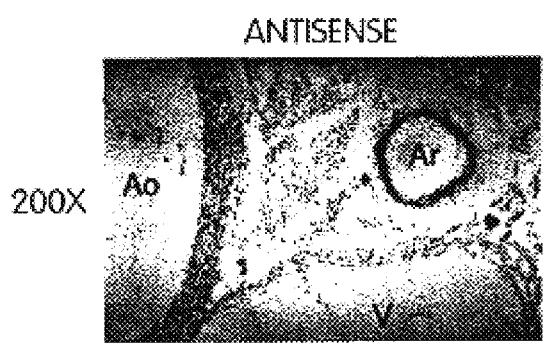
FIG. 5A is a photomicrograph of cells showing in situ hybridization of a r-SmLIM/CRP2 antisense probe to aorta (Ao), small artery (Ar), and vein (V) tissue sections at low magnification (200×).
Figure 5B:
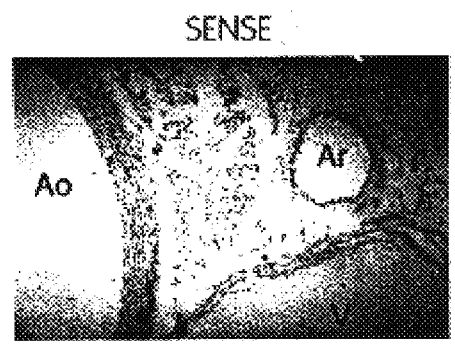
FIG. 5B is photomicrograph of cells showing in situ hybridization of a r-SmLIM/CRP2 sense probe to Ao, Ar, V tissue sections at low magnification (200×).
Figure 5C:
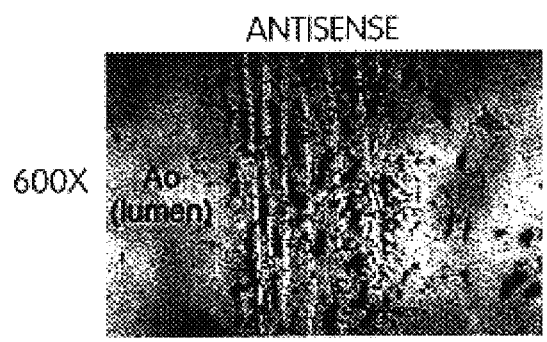
FIG. 5C is photomicrograph of cells showing in situ hybridization of a r-SmLIM/CRP2 antisense probe to Ao tissue at high magnification (600×).
Figure 5D:
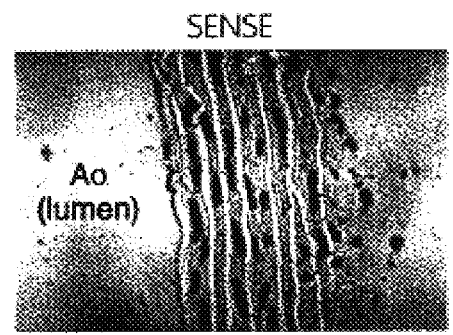
FIG. 5D is photomicrograph of cells showing in situ hybridization of a r-SmLIM/CRP2 sense probe to Ao tissue at high magnification (600×).

To localize r-SmLIM/CRP2 expression within the vessel wall, in situ hybridization was carried out. For each antisense experiment with the r-SmLIM/CRP2 riboprobe (FIGS. 5A and 5C), a corresponding sense (control) experiment (FIGS. 5B and 5D) was performed. FIG. 5A shows intense staining of r-SmLIM/CRP2 in both the aorta (Ao) and a small artery (Ar) nearby. Consistent with Northern analysis data, minimal expression of r-SmLIM/CRP2 was visible in the vena cava (V). A view of the aorta at higher magnification revealed that r-SmLIM/CRP2 expression was limited to smooth muscle cells in the medial layer (FIG. 5C). SmLIM/CRP2 signal expression was absent in skeletal muscle cells. These data indicate that r-SmLIM/CRP2 is expressed preferentially in arterial smooth muscle cells.

Figure 6A:
FIG. 6A is a photograph of a Northern blot assay showing a decrease in r-SmLIM/CRP2 mRNA expression in response to platelet derived growth factor-BB (PDGF-BB) treatment. Rat aortic smooth muscle cells were made quiescent by incubation in low-serum medium (DME plus 0.4% calf serum) for 48 h. Cells were then treated for the indicated times with PDGF-BB (20 ng/ml). Northern analysis was performed with 10 µg of total RNA per lane. After electrophoresis, RNA was transferred to nitrocellulose filters and hybridized with a $^{32}$P-labeled r-SmLIM/CRP2 probe. A single r-SmLIM/CRP2 transcript is visible at 1.0 kb. Filters were hybridized with an 18S-specific probe to verify equivalent sample loading.

Downregulation of r-SmLIM/CRP2 Expression in Vascular Smooth Muscle Cells by Growth Factors and Arterial Wall Injury PDGF-BB is unique among the smooth muscle cell mitogens in its ability to selectively suppress the expression of differentiation markers such as α-actin, smooth muscle myosin heavy chain, and α-tropomyosin in vitro. The effect of PDGF-BB on SmLIM/CRP2 expression was evaluated in cultured vascular smooth muscle cells. r-SmLIM/CRP2 mRNA levels decreased gradually in response to PDGF-BB stimulation (FIG. 6A). A decrease in r-SmLIM/CRP2 expression appeared as early as 4 h after treatment, and a maximal decrease of 80% was obtained at 32 h after treatment.

Figure 6B:
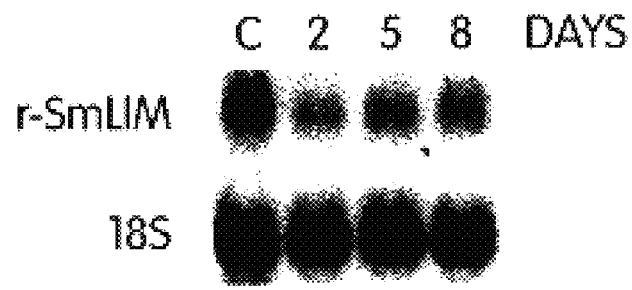
FIG. 6B is a photograph of a Northern blot assay showing a decrease in r-SmLIM/CRP2 mRNA expression after balloon injury in rat carotid arteries. Northern analysis was performed with 20 µg of total RNA per lane at 2, 5, and 8 days after injury. A single r-SmLIM/CRP2 transcript is visible at 1.0 kb. Filters were hybridized with an 18S-specific probe to verify equivalent sample loading.

In response to vessel wall injury, vascular smooth muscle cells undergo a phenotypic change from a differentiated, contractile state to a dedifferentiated, proliferative state. Balloon injury of the rat carotid artery was used to study this change in phenotype in vivo. Since smooth muscle cell proliferation after arterial injury reaches a maximum in the medial layer at 48 h and a maximum in the intimal layer at 96 h (and declines thereafter), r-SmLIM/CRP2 mRNA levels were evaluated at 2, 5, and 8 days after balloon injury of the carotid artery (FIG. 6B). SmLIM/CRP2 mRNA levels decreased by more than 60% after day 2 compared to the control, and remained at this level through day 8. These data indicate that r-SmLIM/CRP2 mRNA decreases in response to smooth muscle cell proliferation and dedifferentiation both in vitro and in vivo.

Developmental Regulation of r-SmLIM/CRP2 mRNA Expression

Figure 7A:
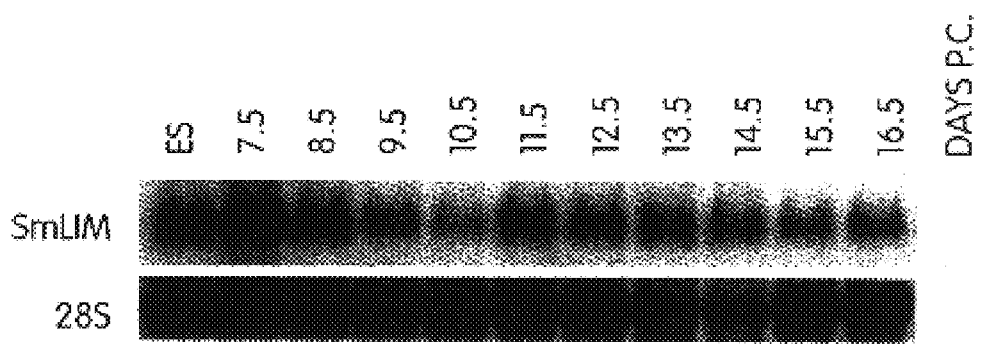
FIG. 7A is a photograph of a Northern blot assay showing expression of r-SmLIM/CRP2. Total RNA isolated from undifferentiated embryonic stem cells (ES) and mouse embryos from days 7.5–16.5 post coitum (p.c.). Northern analysis was performed with 10 µg of total RNA per lane. After electrophoresis, RNA was transferred to nitrocellulose filters and hybridized with a $^{32}$P-labeled r-SmLIM/CRP2 probe. A single r-.SmLIM/CRP2 transcript is visible at 1.0 kb. Filters were hybridized with a 18S ribosomal probe to verify equivalent sample loading.
Figure 7B:
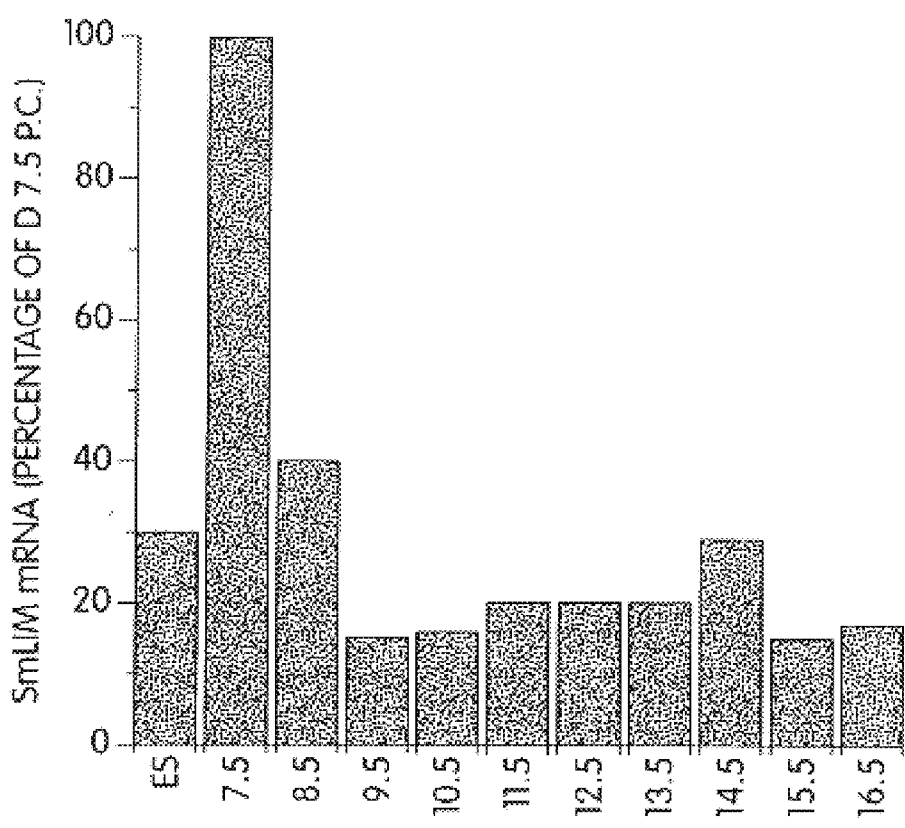
FIG. 7B is a bar graph showing the developmental regulation of SmLIM/CRP2 mRNA expression. The results of the Northern blot assay shown in FIG. 7A are graphically represented. The filters from the Northern blot assay were scanned to quantify the radioactivity.

SmLIM/CRP2 was found to be expressed preferentially in vascular tissue, and its levels are affected by the differentiation state of vascular smooth muscle cells. To determine whether SmLIM/CRP2 expression is regulated during development, total RNA was isolated from undifferentiated embryonic stem cells and whole mouse embryos at days 7.5–16.5 post coitum. SmLIM/CRP2 expression was found to be regulated developmentally (FIGS. 7A and 7B). Expression was highest during the late primitive streak stage (7.5 days p.c.), the point at which the embryonic and extraembryonic circulations begin to develop. SmLIM/CRP2 expression decreased rapidly at subsequent time points. The data normalized to the hybridization signal value at 7.5 days p.c. (FIG. 7B). These data indicate that relative mRNA expression decreased by 40% at 8.5 days p.c. and by approximately 80% at 9.5–16.5 days p.c.

These data indicate that SmLIM/CRP2 expression is regulated developmentally. Expression is highest at day 7.5 p.c. in mouse embryos (FIGS. 7A and 7B) and plateaus by day 9.5 p.c. These early stages represent important points in the development of the mouse heart and vascular systems. At the late primitive streak stage (day 7.5 p.c.), discrete blood islands make their first appearance and amalgamate shortly thereafter to form the yolk sac vasculature. Within the embryo, the early formation of a vasculature is seen at 8.0 days p.c. and amalgamation of the embryonic and extraembryonic circulations at 8.5 days p.c. SmLIM/CRP2 expression was found to be highest in the adult aorta and correlates with the level of smooth muscle cell differentiation, and its embryonic expression is highest during periods critical for vascular development.

Deposit

A plasmid containing DNA encoding h-SmLIM/CRP2 (plasmid containing h-SmLIM/CRP2 cDNA) has been deposited with the American Type Culture Collection (ATCC) under the terms of the Budapest Treaty on the International Recognition of the Deposit of Microorganisms for the Purpose of Patent Procedure on Mar. 13, 1996, and bears the accession number 97470. Applicants' assignee, President and Fellows of Harvard College, acknowledges its duty to replace the deposit should the depository be unable to furnish a sample when requested due to the condition of the deposit before the end of the term of a patent issued hereon, and its responsibility to notify the ATCC of the issuance of such a patent, at which time the deposit will be made available to the public. Prior to that time, the deposit will be made available to the Commissioner of Patents under the terms of CFR §1.14 and 35 U.S.C. §112.

Methods of Therapy

The invention is based on the identification and characterization of a SmLIM/CRP2 polypeptide which is expressed preferentially in aortic smooth muscle cells. In vivo, SmLIM/CRP2 mRNA levels were found to decrease as vascular smooth muscle cells changed from a quiescent to a proliferative phenotype in response to vascular injury. Thus, administering SmLIM/CRP2 polypeptide or increasing expression of a SmLIM/CRP2-encoding DNA, e.g., by stimulating the SmLIM/CRP2 promoter or by introducing additional copies of SmLIM/CRP2-encoding DNA, in vascular smooth muscle cells which are injured or at risk of being injured can inhibit proliferation by promoting a quiescent, differentiated state.

An animal, e.g., a human patient, with arteriosclerosis or at risk of developing arteriosclerosis (and therefore in need of inhibition of arteriosclerosis or inhibition of vascular smooth muscle cell proliferation), may be identified using standard medical procedures, such as angiographic visualization of the lumen of a blood vessel, Doppler probes for measuring velocity and volume of blood flow, stress test, and ultrasound to detect arteriosclerotic plaques. Other patients in need of inhibition of arteriosclerosis or vascular smooth muscle cell proliferation are those with angina or stroke. Improvement of the patient's condition during and after therapy may be similarly monitored. Patients undergoing invasive vascular procedures, in particular balloon angioplasty, are also at risk for developing arteriosclerosis.

Angioplasty, used to treat arteriosclerosis, involves the insertion of catheters, e.g., balloon catheters, through an occluded region of a blood vessel in order to expand the lumenal opening. However, the aftermath of angioplasty may be problematic. Restenosis, or closing of the vessel, can occur as a consequence of injury, e.g., mechanical abrasion associated with the angioplasty treatment. This restenosis is believed to be caused by proliferation of smooth muscle cells stimulated by vascular injury. Other anatomical disruptions or mechanical disturbances of a blood vessel, e.g., attributable to laser angioplasty, coronary artery surgery, atherectomy and coronary artery stents, may also cause vascular injury and subsequent proliferation of smooth muscle cells. A SmLIM/CRP2 polypeptide, DNA encoding a SmLIM/CRP2 polypeptide, or compositions which stimulate expression from the SmLIM/CRP2 promoter may administered to increase the level of SmLIM/CRP2 polypeptide in the injured vascular tissue and thus inhibit the proliferation of smooth muscle cells.

SmLIM/CRP2 polypeptides may be administered to the patient intravenously in a pharmaceutically acceptable carrier such as physiological saline. Standard methods for intracellular delivery of peptides can be used, e.g. packaged in liposomes. Such methods are well known to those of ordinary skill in the art. It is expected that an intravenous dosage of approximately 1 to 100 µmoles of the polypeptide of the invention would be administered per kg of body weight per day. The compositions of the invention are useful for parenteral administration, such as intravenous, subcutaneous, intramuscular, and intraperitoneal routes.

Gene Therapy and Antisense Therapy

DNA (e.g., SmLIM/CRP2-encoding DNA, vascular cell-specific promoters, and vectors) of the invention may be introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others. For example, the DNA of the invention under the control of a strong constitutive promoter may be administered locally to a blood vessel during balloon angioplasty using an adenovirus delivery system.

A vascular cell-specific promoter may be used to direct the expression of SmLIM/CRP2 or genes other than SmLIM/CRP2. Thus, vascular diseases may be treated by administering a vascular cell-specific promoter of the invention operatively linked to a sequence encoding a heterologous polypeptide, e.g., a SmLIM/CRP2 promoter linked to DNA encoding a growth inhibitor gene such as Rb, p21 or p18.

The invention can be used for gene therapy treatment of vascular diseases. The DNA of the invention can be used alone or as part of a vector to express heterologous genes, e.g., genes which encode proteins other than SmLIM/CRP2, in cells of the blood vessel wall, i.e., vascular smooth muscle cells, for gene therapy of vascular diseases such as arteriosclerosis. The DNA or vector containing a sequence encoding a polypeptide of interest is introduced into vascular smooth muscle cells which in turn produce the polypeptide of interest. For example, sequences encoding t-PA (Pennica et al., 1982, Nature 301:214), p21 cell cycle inhibitor (El-Deiry et al., 1993, Cell 75:817–823), or nitric oxide synthase (Bredt et al., 1990, Nature 347:768–770) may be operably linked to the vascular smooth muscle cell-specific promoter sequences of the invention and expressed in smooth muscle cells. For example, thrombolytic agents can be expressed under the control of the SmLIM/CRP2 promoter sequences for expression by vascular smooth muscle cells in blood vessels, e.g., vessels occluded by aberrant blood clots. Other heterologous proteins, e.g., proteins which inhibit smooth muscle cell proliferation, e.g., interferon-γ and atrial natriuretic polypeptide, may be specifically expressed in vascular smooth muscle cells to ensure the delivery of these therapeutic peptides to an arteriosclerotic lesion or an area at risk of developing an arteriosclerotic lesion, e.g., an injured blood vessel.

The SmLIM/CRP2 promoter sequences of the invention may also be used in gene therapy to promote angiogenesis to treat diseases such as peripheral vascular disease or coronary artery disease. For example, the promoter sequences can be operably linked to heterologous sequences encoding cellular growth factors which promote angiogenesis, e.g., VEGF, acidic fibroblast growth factor, or basic fibroblast growth factor.

According to the invention, the DNA of the invention is located sufficiently close to the coding sequence to be transcribed that it functions to direct expression of the polypeptide in vascular smooth muscle cell. For example, the promoter sequences are preferably located 5' to the transcription start site.

The DNA of the invention may also be used in methods of antisense therapy. Antisense therapy may be carried out by administering to an animal, e.g., a human patient, DNA containing the vascular smooth muscle cell-specific promoter sequences of the invention, e.g., SEQ ID NO:16, operably linked to a DNA sequence, i.e., an antisense template, which is transcribed into an antisense RNA. The antisense RNA may be a short (generally at least 10, preferably at least 14 nucleotides, and up to 100 or more nucleotides) nucleotide sequence formulated to be complementary to all or a portion of a specific mRNA sequence. The antisense template is preferably located downstream from the promoter sequences of the invention. A poly A tail is typically located at the end of the antisense sequence to signal the end of the sequence. Standard methods relating to antisense technology have been described (Melani et al., Cancer Res. 51:2897–2901, 1991). Following transcription of the DNA sequence into antisense RNA, the antisense RNA binds to its target mRNA molecules within a cell, thereby inhibiting translation of the mRNA and down-regulating expression of the protein encoded by the mRNA.

The expression of vascular smooth muscle cell proteins may be inhibited using antisense therapy. For example, the DNA of the invention can be operably linked to antisense templates which are transcribed into antisense RNA capable of inhibiting the expression of the smooth muscle cell proteins.

For gene therapy or antisense therapy, the claimed DNA may be introduced into target cells of an animal, e.g., a patient, using standard vectors and/or gene delivery systems. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy or antisense therapy may also be accomplished using a biolistic delivery system, such as that described by Williams et al., 1991, Proc. Natl. Acad. Sci. U.S.A. 88:2726–2729. Standard methods for transfecting cells with isolated DNA are well known to those skilled in the art of molecular biology. Gene therapy and antisense therapy to prevent or decrease the development of arteriosclerosis may be carried out by directly administering the claimed DNA to a patient or by transfecting vascular smooth cells with the claimed DNA ex vivo and infusing the transfected cells into the patient.

DNA or transfected cells may be administered in a pharmaceutically acceptable carrier. Pharmaceutically acceptable carriers are biologically compatible vehicles which are suitable for administration to an animal, e.g., physiological saline. A therapeutically effective amount is an amount of the DNA of the invention which is capable of producing a medically desirable result in a treated animal. As is well known in the medical arts, dosages for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is from approximately $10^6$ to $10^{22}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery. The preferred form of the composition to be administered depends on the intended mode of administration and therapeutic application. For example, SmLIM/CRP2 polypeptides or SmLIM/CRP2-encoding DNA may be administered in solution form through a catheter port or as a coating on the surface of a catheter, e.g., the balloon portion of a catheter used for balloon angioplasty.

Drugs which stimulate the SmLIM/CRP2 promoter may also be administered as described above to increase the level of expression of SmLIM/CRP2 in vascular tissue, e.g., arterial smooth muscle cells. Such drugs can be identified by contacting the SmLIM/CRP2 promoter linked to a reporter gene with a candidate compound and measuring the level of expression of the reporter gene in the presence and absence of the compound. An increased level of expression in the presence of the compound compared to that in its absence indicates that the compound stimulates the SmLIM/CRP2 promoter.

Methods of Diagnosis

The invention includes a method of detecting injury in a sample of vascular tissue. A depressed level of SmLIM/CRP2 polypeptide or transcript compared to the level in normal control vascular cells would predict a high degree of smooth muscle cell proliferation indicative of vascular tissue injury, e.g., restenosis. The diagnostic method of the invention is carried out by determining the level of SmLIM/CRP2 gene expression in a tissue, e.g, a vascular biopsy obtained at atherectomy. The level of gene expression may be measured using methods known in the art, e.g., in situ hybridization, Northern blot analysis, or Western blot analysis using SmLIM/CRP2-specific monoclonal or polyclonal antibodies. A decrease in the level of SmLIM/CRP2 expression in the test sample of tissue compared to the level per cell in uninjured control vascular tissue indicates the presence of a vascular injury in the test sample. It also indicates that the patient is a candidate for treatment with a therapeutic agent which increases the amount of SmLIM/CRP2 in the affected vascular smooth muscle cells. For example, tissue obtained at atherectomy could be tested for SmLIM/CRP2 expression, e.g., the level of SmLIM/CRP2 transcript or polypeptide. A depressed level of SmLIM/CRP2 transcript or polypeptide (compared to normal tissue) correlates with a high degree of smooth muscle cell proliferation indicating a high probability of restenosis. Such diagnostic procedures are useful to identify patients in need of therapeutic intervention to reduce or prevent restenosis.

Cells and antibodies

Cells are transfected with the SmLIM/CRP2-encoding DNA using standard methods. Cells, e.g, vascular smooth muscle cells, expressing a SmLIM/CRP2 polypeptide, may be administered to an animal locally or systemically using intravenous, subcutaneous, intramuscular, and intraperitoneal delivery methods.

Alternatively, procaryotic or eucaryotic cells in culture can be transfected with the DNA of the invention operatively linked to expression control sequences appropriate for high-level expression in the cell. Such cells are useful for producing large amounts of the SmLIM/CRP2 polypeptide, which can be purified and used, e.g., as a therapeutic or for raising anti-SmLIM/CRP2 antibodies.

The anti-SmLIM/CRP2 antibodies useful in the present invention can be obtained by techniques well known in the art. Such antibodies can be polyclonal or monoclonal. Polyclonal antibodies can be obtained, for example, by the methods described in Ghose et al., Methods in Enzymology, Vol. 93, 326–327, 1983. For example, a SmLIM/CRP2 polypeptide, or an antigenic fragment thereof, can be used as the immunogen to stimulate the production of SmLIM/CRP2-reactive polyclonal antibodies in the antisera of animals such as rabbits, goats, sheep, rodents and the like.

The monoclonal antibodies useful in the present invention can be obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for a SmLIM/CRP2 polypeptide. Preferably, the antibody will have an affinity of at least about $10^8$ liters/mole and more preferably, an affinity of at least about $10^9$ liters/mole. The use of such monoclonal antibodies provides a means of obtaining greater sensitivity in the assays of the present invention compared with the use of polyclonal antibodies.

Other embodiments are within the claims.

What is claimed is:

1. An isolated DNA molecule comprising the nucleotide sequence of SEQ ID NO: 16, wherein said nucleotide sequence regulates arterial smooth muscle cell-specific transcription of a polypeptide-encoding sequence to which it is operably linked.

2. The DNA molecule of claim 1, wherein said nucleotide sequence is operably linked to a heterologous polypeptide-encoding sequence.

3. An isolated DNA molecule, comprising a first DNA sequence comprising SEQ ID NO: 16, operably linked to a second DNA sequence encoding a polypeptide other than SmLIM/CRP2, wherein said first DNA sequence directs transcription of said second DNA sequence in a vascular smooth muscle cell.

4. A vector comprising the DNA molecule of claim 3.

5. A method of directing vascular smooth muscle cell-specific expression of a polypeptide, comprising introducing into a vascular smooth muscle cell the vector of claim 4, and maintaining said cell under conditions suitable for polypeptide expression.

6. An isolated vascular smooth muscle cell comprising the vector of claim 4.

7. The DNA molecule of claim 3, wherein transcription of said second DNA sequence is at least 2-fold greater in a vascular smooth muscle cell compared to in a non-vascular smooth muscle cell.

8. An isolated DNA molecule comprising a DNA sequence which hybridizes under conditions of hybridization at 42 degrees in the presence of 50% formamide followed by a wash in 0.1×SSC at 65 degrees to the nucleotide sequence of SEQ ID NO: 16, wherein said DNA sequence regulates arterial smooth muscle cell-specific transcription of a polypeptide-encoding sequence to which it is operably linked.

9. An isolated DNA molecule comprising a DNA sequence comprising nucleotides −39 to −74 of SEQ ID NO: 16, wherein said DNA sequence regulates arterial smooth muscle cell-specific transcription of a polypeptide-encoding sequence to which it is operably linked.

10. The DNA molecule of claim 9, wherein said DNA sequence is operably linked to a heterologous polypeptide-encoding sequence.

11. A method of directing vascular smooth muscle cell-specific expression of a polypeptide comprising introducing into an arterial smooth muscle cell the DNA molecule of claim 10, wherein said heterologous polypeptide-encoding sequence is expressed at detectable levels in said arterial smooth muscle cell.

12. An isolated DNA molecule comprising a first DNA sequence comprising nucleotides −39 to −74 of SEQ ID NO: 16, operably linked to a second DNA sequence encoding a polypeptide other than SmLIM/CRP2, wherein said first DNA sequence directs transcription of said second DNA sequence in a vascular smooth muscle cell.

13. A vector comprising the DNA molecule of claim 12.

14. An isolated vascular smooth muscle cell comprising the vector of claim 13.

15. The DNA molecule of claim 12, wherein transcription of said second DNA sequence is at least 2-fold greater in a vascular smooth muscle cell compared to in a non-vascular smooth muscle cell.

16. An isolated DNA molecule comprising a DNA sequence which hybridizes under conditions of hybridization at 42 degrees in the presence of 50% formamide followed by a wash in 0.1×SSC 65 degrees to nucleotides −39 to −74 of SEQ ID NO: 16, wherein said sequence regulates arterial smooth muscle cell-specific transcription of a polypeptide-encoding sequence to which it is operable linked.

* * * * *

UNITED STATES PATENT AND TRADEMARK OFFICE
CERTIFICATE OF CORRECTION

PATENT NO. : 6,258,557 B1
DATED : July 10, 2001
INVENTOR(S) : Mu-En Lee, Edgar Haber, Mukesh Jain and Shaw-Fang Yet Page 1 of 1

It is certified that error appears in the above-identified patent and that said Letters Patent is hereby corrected as shown below:

Column 2,
Line 41, after "at about", delete "650°" and insert -- 65° --.

Signed and Sealed this

Fifth Day of March, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 193 amino acids
      (B) TYPE: amino acid
      (D) TOPOLOGY: linear (ii) MOLECULE TYPE: protein (xi) SEQUENCE DESCRIPTION: SEQ ID NO:1:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Ser Phe His Arg
                20                  25                  30

Cys Cys Phe Leu Cys Met Val Cys Arg Lys Asn Leu Asp Ser Thr Thr
            35                  40                  45

Val Ala Ile His Asp Glu Glu Ile Tyr Cys Lys Ser Cys Tyr Gly Lys
        50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Val Gln
                85                  90                  95

Pro His Arg Pro Thr Thr Asn Pro Asn Thr Ser Lys Phe Ala Gln Lys
                100                 105                 110

Tyr Gly Ala Glu Lys Cys Ser Arg Cys Gly Asp Ser Val Tyr Ala
            115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Lys Val His Ala
                180                 185                 190

Gln
```

(2) INFORMATION FOR SEQ ID NO:2:

(i) SEQUENCE CHARACTERISTICS:
        (A) LENGTH: 741 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:2:

```
ATGCCTGTCT GGGGAGGTGG AAACAAGTGT GGGGCCTGTG GGAGGACCGT GTACCACGCA      60
GAAGAGGTGC AGTGTGATGG CAGGAGCTTC CACCGCTGCT GCTTTCTCTG CATGGTTTGC     120
AGGAAAAATT TAGATAGCAC AACAGTGGCA ATTCACGATG AAGAGATCTA CTGCAAATCC     180
TGCTACGGAA AGAAGTATGG GCCAAAAGGC TACGGTTATG GCCAGGGCGC TGGCACGCTT     240
AACATGGACC GTGGCGAGAG GCTGGGCATC AAACCAGAGA GTGTTCAGCC TCACAGGCCT     300
ACAACAAATC CAAACACTTC TAAATTTGCT CAGAAATATG GAGGTGCTGA GAAGTGTTCC     360
AGATGTGGGG ATTCTGTATA TGCTGCCGAG AAGATAATTG GAGCTGGAAA GCCCTGGCAC     420
AAAAACTGTT TCCGATGTGC AAAGTGTGGG AAGAGTCTTG AATCAACAAC TCTGACTGAA     480
AAAGAAGGTG AAATCTATTG TAAAGGATGC TATGCAAAGA ACTTTGGGCC CAAGGGATTT     540
GGCTATGGCC AAGGAGCAGG GGCTCTTGTT CATGCCCAGT AAGATGTAAA CCCTGAACTA     600
AACATCACAC ACTGAGAATC TCTTCATAAT CTAGGCACAG ATAATCTTTA ACCCGGAATT     660
CCGCCGATAC TGACGGGCTC CAGGAGTCGT CGCCACCAAG CCGAATTCCA GCACACTGGC     720
GGCCGTTACT AGTGGATCCG A                                               741
```

(2) INFORMATION FOR SEQ ID NO:3:

(i) SEQUENCE CHARACTERISTICS:
        (A) LENGTH: 427 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:3:

```
TGAGGAATGC AGCTCTTTCG CGACAGGAAA GCTGCGGATT CCAGAAGCCG GGATTCTGAC      60

CAGAGACTAT CTGCACCGGG GAGTCCTGCA CCCCGAGCTA ACATATGGCG TTTGTGCAGT     120

AAAAGGGTGG CGGGAATCCC ACGGGGCGAC ACCGGATCTC GCTGGCTCCG GGCCGATCCT     180

GAGTGCTCCG GACGTCCCGG GACCGCGGGT AGGAGCAGCC GAGACGTGGG AGACTCGGAC     240

GCGGGAAGCC GCAGGAAGAG GCGGATTCCG GTCTTTTTGT CTCGGGGCCA GAGCACGAAA     300

CCCGCATCGG ATCCCCGAGC TCACGCCGGG CGGAGACCAT CGCACACCCG AGGGGCATGA     360

CCGATGGCTG AGTCGGAACA AGCCACGCCC AACATAAGTC TTTAAAAGCG GGCACACGCG     420

TCCCGCC                                                               427
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
GAGTCTTCAC CATGCCGAAC                                                  20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

```
CTCTCCCACC CCAAAAATAG                                                  20
```

(2) INFORMATION FOR SEQ ID NO:6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:6:

```
Glu Gln Lys Leu Ile Ser Glu Glu Asp
 1               5
```

(2) INFORMATION FOR SEQ ID NO:7:

(i) SEQUENCE CHARACTERISTICS:
        (A) LENGTH: 880 base pairs

-continued (B) TYPE: nucleic acid
(C) STRANDEDNESS: both
(D) TOPOLOGY: linear (ii) MOLECULE TYPE: DNA (ix) FEATURE:
(A) NAME/KEY: Coding Sequence
(B) LOCATION: 55...633
(D) OTHER INFORMATION:

(xi) SEQUENCE DESCRIPTION: SEQ ID NO:7:

```
ACGAGCTAGA CCTCCCTAGC TCCGCCCGCC GCGTGCTCCC GCCTCCCACT CGGA ATG       57
                                                             Met
                                                             1

CCT GTC TGG GGG GGT GGA AAT AAG TGC GGG GCC TGC GGG AGA ACC GTG     105
Pro Val Trp Gly Gly Gly Asn Lys Cys Gly Ala Cys Gly Arg Thr Val
            5                   10                  15

TAC CAC GCT GAA GAG GTG CAG TGT GAT GGG CGG ACG TTC CAC CGC TGC     153
Tyr His Ala Glu Glu Val Gln Cys Asp Gly Arg Thr Phe His Arg Cys
            20                  25                  30

TGC TTT CTG TGC ATG GTT TGC AGG AAA AAT TTA GAC AGC ACA ACA GTG     201
Cys Phe Leu Cys Met Val Cys Arg Lys Asn Leu Asp Ser Thr Thr Val
35                  40                  45

GCA ATT CAT GAT GAA GAG ATC TAC TGC AAA TCA TGC TAC GGA AAG AAG     249
Ala Ile His Asp Glu Glu Ile Tyr Cys Lys Ser Cys Tyr Gly Lys Lys
50                  55                  60                  65

TAT GGA CCA AAA GGC TAT GGT TAT GGC CAG GGC GCT GGC ACG CTC AAC     297
Tyr Gly Pro Lys Gly Tyr Gly Tyr Gly Gln Gly Ala Gly Thr Leu Asn
            70                  75                  80

ATG GAC CGT GGT GAG AGG CTG GGC ATC AAG CCA GAG AGT GCT CAA CCT     345
Met Asp Arg Gly Glu Arg Leu Gly Ile Lys Pro Glu Ser Ala Gln Pro
            85                  90                  95

CAC AGG CCT ACA ACA AAT CCA AAC ACT TCT AAA TTT GCC CAG AAA TAT     393
His Arg Pro Thr Thr Asn Pro Asn Thr Ser Lys Phe Ala Gln Lys Tyr
            100                 105                 110

GGA GGT GCT GAG AAG TGC TCC AGA TGT GGG GAT TCT GTG TAT GCT GCT     441
Gly Gly Ala Glu Lys Cys Ser Arg Cys Gly Asp Ser Val Tyr Ala Ala
            115                 120                 125

GAG AAG ATC ATT GGA GCT GGA AAG CCC TGG CAC AAA AAC TGT TTC CGA     489
Glu Lys Ile Ile Gly Ala Gly Lys Pro Trp His Lys Asn Cys Phe Arg
130                 135                 140                 145

TGT GCC AAG TGT GGG AAG AGT CTG GAG TCT ACA ACT CTG ACT GAG AAG     537
Cys Ala Lys Cys Gly Lys Ser Leu Glu Ser Thr Thr Leu Thr Glu Lys
            150                 155                 160

GAA GGT GAA ATC TAC TGT AAA GGG TGC TAC GCA AAG AAC TTT GGG CCC     585
Glu Gly Glu Ile Tyr Cys Lys Gly Cys Tyr Ala Lys Asn Phe Gly Pro
            165                 170                 175

AAG GGA TTC GGC TAT GGT CAA GGA GCA GGG GCC CTT GTT CAT GCT CAG T   634
Lys Gly Phe Gly Tyr Gly Gln Gly Ala Gly Ala Leu Val His Ala Gln
            180                 185                 190

AGTGGTGTAA ACCCAGTAAG CATGGCAAAG AACCTCCATT AATGTGGATG GCCTTACCGC     694

ACTCAGGCTG TGCATCGGCC AGCACTCAGC ACTGTGTAGC ACACACGCTA TGTGCACAAT     754

CGGGCTGGAC AGGAAGCACT ACACTCTCCT GCCCATCCGC TAACGTTTAA GAACGTTCTT     814

TTACATTTGG AATAAAATTT TGGTTTGATT TGAAAAAAAA AAAAAAAAAA AAAAAAAAAA     874

AAAAAA                                                                 880
```

(2) INFORMATION FOR SEQ ID NO:8:

(i) SEQUENCE CHARACTERISTICS:

(A) LENGTH: 193 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

```
Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
            20                  25                  30

Cys Cys Phe Leu Cys Met Val Cys Arg Lys Asn Leu Asp Ser Thr Thr
        35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Ala Gln
                85                  90                  95

Pro His Arg Pro Thr Thr Asn Pro Asn Thr Ser Lys Phe Ala Gln Lys
            100                 105                 110

Tyr Gly Gly Ala Glu Lys Cys Ser Arg Cys Gly Asp Ser Val Tyr Ala
        115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln
```

(2) INFORMATION FOR SEQ ID NO:9:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:9:

```
Met Pro Asn Trp Gly Gly Gly Lys Lys Cys Gly Val Cys Gln Lys Thr
 1               5                  10                  15

Val Tyr Phe Ala Glu Glu Val Gln Cys Glu Gly Asn Ser Phe His Lys
            20                  25                  30

Ser Cys Phe Leu Cys Met Val Cys Lys Lys Asn Leu Asp Ser Thr Thr
        35                  40                  45

Val Ala Val His Gly Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Ser Met Asp Lys Gly Glu Ser Leu Gly Ile Lys His Glu Glu Ala Pro
                85                  90                  95

Gly His Arg Pro Thr Thr Asn Pro Asn Ala Ser Lys Phe Ala Gln Lys
```

```
                   100                 105                 110
Ile Gly Gly Ser Glu Arg Cys Pro Arg Cys Ser Gln Ala Val Tyr Ala
            115                 120                 125
Ala Glu Lys Val Ile Gly Ala Gly Lys Ser Trp His Lys Ser Cys Phe
130                 135                 140
Arg Cys Ala Lys Cys Gly Lys Gly Leu Glu Ser Thr Thr Leu Ala Asp
145                 150                 155                 160
Lys Asp Gly Glu Ile Tyr Cys Lys Gly Cys Tyr Ala Lys Asn Phe Gly
            165                 170                 175
Pro Lys Gly Phe Gly Phe Gly Gln Gly Ala Gly Ala Leu Val His Ser
            180                 185                 190
Glu
```

(2) INFORMATION FOR SEQ ID NO:10:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:10:

```
Met Pro Asn Trp Gly Gly Gly Lys Lys Cys Gly Val Cys Gln Lys Thr
1               5                  10                  15
Val Tyr Phe Ala Glu Glu Val Gln Cys Glu Gly Asn Ser Phe His Lys
            20                  25                  30
Ser Cys Phe Leu Cys Met Val Cys Lys Lys Asn Leu Asp Ser Thr Thr
            35                  40                  45
Val Ala Val His Gly Glu Glu Ile Tyr Cys Lys Ser Cys Tyr Gly Lys
50                  55                  60
Lys Tyr Gly Pro Lys Gly Tyr Gly Tyr Gly Gln Gly Ala Gly Thr Leu
65                  70                  75                  80
Ser Thr Asp Lys Gly Glu Ser Leu Gly Ile Lys Gly Glu Glu Ala Pro
            85                  90                  95
Gly His Arg Pro Thr Thr Asn Pro Asn Ala Ser Lys Phe Ala Gln Lys
            100                 105                 110
Ile Gly Gly Ser Glu Arg Cys Pro Arg Cys Ser Gln Ala Val Tyr Ala
            115                 120                 125
Ala Glu Lys Val Ile Gly Ala Gly Lys Ser Gln His Lys Ala Cys Phe
130                 135                 140
Arg Cys Ala Lys Cys Gly Lys Gly Leu Glu Ser Thr Thr Leu Ala Asp
145                 150                 155                 160
Lys Asp Gly Glu Ile Tyr Cys Lys Gly Cys Tyr Ala Lys Asn Phe Gly
            165                 170                 175
Pro Lys Gly Phe Gly Phe Gly Gln Gly Ala Gly Ala Leu Val His Ser
            180                 185                 190
Glu
```

(2) INFORMATION FOR SEQ ID NO:11:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:11:

```
Met Pro Asn Trp Gly Gly Gly Ala Lys Cys Gly Ala Cys Asp Lys Thr
 1               5                  10                  15

Val Tyr Gly Ala Glu Glu Ile Gln Cys Asn Gly Arg Ser Phe His Lys
                20                  25                  30

Thr Cys Phe His Cys Met Ala Cys Arg Lys Ala Leu Asp Ser Thr Thr
            35                  40                  45

Val Ala Ala His Glu Ser Glu Ile Tyr Cys Lys Val Cys Tyr Gly Arg
 50                  55                  60

Lys Tyr Gly Pro Lys Gly Ile Gly Phe Gly Gln Gly Ala Gly Cys Leu
 65                  70                  75                  80

Ser Thr Asp Thr Gly Glu His Leu Gly Leu Gln Phe Gln Gln Ser Pro
                85                  90                  95

Lys Pro Ala Arg Ala Ala Thr Thr Ser Asn Pro Ser Lys Phe Ser Ala
               100                 105                 110

Lys Phe Gly Glu Ser Glu Lys Cys Pro Arg Cys Gly Lys Ser Val Tyr
            115                 120                 125

Ala Ala Glu Lys Val Met Gly Gly Lys Pro Trp His Lys Thr Cys
130                 135                 140

Phe Pro Cys Ala Ile Cys Gly Lys Ser Leu Glu Ser Thr Asn Val Thr
145                 150                 155                 160

Asp Lys Asp Gly Glu Leu Tyr Cys Lys Val Cys Tyr Ala Lys Asn Phe
                165                 170                 175

Gly Pro Thr Gly Ile Gly Phe Gly Gly Leu Thr His Gln Val Glu Lys
                180                 185                 190

Lys Glu
```

(2) INFORMATION FOR SEQ ID NO:12:

(i) SEQUENCE CHARACTERISTICS:
        (A) LENGTH: 194 amino acids
        (B) TYPE: amino acid
        (D) TOPOLOGY: linear (ii) MOLECULE TYPE: protein (ix) FEATURE:
        (D) OTHER INFORMATION: Xaa is any amino acid or unknown.

(xi) SEQUENCE DESCRIPTION: SEQ ID NO:12:

```
Met Pro Xaa Trp Gly Gly Gly Xaa Lys Cys Gly Xaa Cys Xaa Xaa Thr
 1               5                  10                  15

Val Tyr Xaa Ala Glu Glu Val Gln Cys Xaa Gly Xaa Xaa Phe His Xaa
                20                  25                  30

Xaa Cys Phe Xaa Cys Met Xaa Cys Xaa Lys Xaa Leu Asp Ser Thr Thr
            35                  40                  45

Val Ala Xaa His Xaa Xaa Glu Ile Tyr Cys Lys Xaa Cys Tyr Gly Xaa
 50                  55                  60

Lys Tyr Gly Pro Lys Gly Xaa Gly Tyr Gly Trp Gly Ala Gly Xaa Leu
 65                  70                  75                  80

Xaa Xaa Asp Xaa Gly Glu Xaa Leu Gly Xaa Xaa Xaa Xaa Xaa Xaa Xaa
                85                  90                  95

Xaa Xaa Xaa Arg Xaa Xaa Thr Xaa Xaa Asn Xaa Ser Lys Phe Xaa Xaa
               100                 105                 110

Lys Xaa Gly Xaa Xaa Glu Xaa Cys Xaa Arg Cys Xaa Xaa Xaa Val Tyr
            115                 120                 125
```

```
Ala Ala Glu Lys Xaa Xaa Gly Xaa Gly Lys Xaa Trp His Lys Xaa Cys
    130             135                 140

Phe Xaa Cys Ala Xaa Cys Gly Lys Xaa Leu Glu Ser Thr Xaa Xaa Xaa
145             150                 155                     160

Xaa Lys Xaa Gly Glu Xaa Tyr Cys Lys Xaa Cys Tyr Ala Lys Asn Phe
                165                 170                 175

Gly Pro Xaa Gly Xaa Gly Xaa Gly Xaa Xaa Xaa Xaa Xaa Xaa Xaa Xaa
            180                 185                 190

Xaa Xaa (2) INFORMATION FOR SEQ ID NO:13:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:13:

Met Pro Val Trp Gly Gly Gly Asn Lys Cys Gly Ala Cys Gly Arg Thr
1               5                   10                  15

Val Tyr His Ala Glu Glu Val Gln Cys Asp Gly Arg Thr Phe His Arg
            20                  25                  30

Cys Cys Phe Leu Cys Met Val Cys Arg Lys Asn Leu Asp Ser Thr Thr
                35                  40                  45

Val Ala Ile His Asp Glu Glu Ile Tyr Cys Lys Ser Cys Tyr Gly Lys
    50                  55                  60

Lys Tyr Gly Pro Lys Gly Tyr Gly Tyr Gly Gln Gly Ala Gly Thr Leu
65                  70                  75                  80

Asn Met Asp Arg Gly Glu Arg Leu Gly Ile Lys Pro Glu Ser Ala Gln
                85                  90                  95

Pro His Arg Pro Thr Thr Asn Pro Asn Thr Ser Lys Phe Ala Gln Lys
                100                 105                 110

Tyr Gly Gly Ala Glu Lys Cys Ser Arg Cys Gly Asp Ser Val Tyr Ala
            115                 120                 125

Ala Glu Lys Ile Ile Gly Ala Gly Lys Pro Trp His Lys Asn Cys Phe
    130                 135                 140

Arg Cys Ala Lys Cys Gly Lys Ser Leu Glu Ser Thr Thr Leu Thr Glu
145                 150                 155                 160

Lys Glu Gly Glu Ile Tyr Cys Lys Gly Cys Tyr Ala Lys Asn Phe Gly
                165                 170                 175

Pro Lys Gly Phe Gly Tyr Gly Gln Gly Ala Gly Ala Leu Val His Ala
            180                 185                 190

Gln (2) INFORMATION FOR SEQ ID NO:14:

(i) SEQUENCE CHARACTERISTICS:
        (A) LENGTH: 840 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:14:

AGTCTCCGGA TCCGCCCGCG GCTTTCCTCG GTCAGACCTC GTTAGCTCCG CCCGCCGCGT     60
```

```
GCTCCCTCCT CCCACTCGGA ATGCCTGTCT GGGGCGGTGG AAATAAGTGC GGGGCCTGCG      120

GGAGAACCGT GTACCACGCG GAAGAGGTGC AGTGCGATGG GCGGACGTTC CATCGCTGCT      180

GCTTCCTGTG CATGGTTTGC AGGAAAAATT TAGACAGCAC AACAGTGGCG ATTCATGATG      240

AAGAGATCTA CTGCAAATCC TGCTACGGAA AGAAGTATGG ACCAAAAGGC TATGGTTATG      300

GCCAGGGCGC TGGCACGCTC AACATGGACC GCGGTGAGAG ACTGGGCATC AAGCCAGAGA      360

GTGCTCAACC TCACAGGCCT ACGACAAATC CAAACACTTC TAAATTTGCC CAGAAATATG      420

GAGGAGCTGA GAAGTGTTCC AGGTGTGGGG ATTCCGTGTA TGCTGCGGAG AAGATCATTG      480

GAGCTGGGAA GCCCTGGCAC AAAAACTGTT TCCGGTGTGC CAAGTGTGGG AAGAGTCTGG      540

AGTCTACAAC TCTGACTGAG AAAGAAGGCG AAATCTACTG TAAAGGGTGC TACGCAAAGA      600

ACTTTGGGCC CAAGGGATTT GGCTATGGTC AAGGGGCAGG GGCCCTTGTT CATGCTCAGT      660

AATGGTGTGA ACCAGTAAGC ACGACAGAGA ATCTCCATTA CCAAACTGCA GATGGCGTTT      720

ATGGCGCTCA CTACTGTGAA ACAGCCAGCA CTTGGCACTG GCATCACCG AGCTGCCTGT      780

GGGGGCTGGA CCGACAGCGC TGCACTCTCC CGCCCACTCA CTAGCGTCTA AGAGCATTCT      840
```

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:15:

Lys Lys Tyr Gly Pro Lys
1             5

(2) INFORMATION FOR SEQ ID NO:16:

(i) SEQUENCE CHARACTERISTICS:
        (A) LENGTH: 522 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:16:

```
TGAGGAATGC AGCTCTTTCG CGACAGGAAA GCTGCGGATT CCAGAAGCCG GGATTCTGAC       60

CAGAGACTAT CTGCACCGGG GAGTCCTGCA CCCCGAGCTA ACATATGGCG TTTGTGCAGT      120

AAAAGGGTGG CGGGAATCCC ACGGGGCGAC ACCGGATCTC GCTGGCTCCG GGCCGATCCT      180

GAGTGCTCCG GACGTCCCGG GACCGCGGGT AGGAGCAGCC GAGACGTGGG AGACTCGGAC      240

GCGGAAGCC GCAGGAAGAG GCGGATTCCG GTCTTTTTGT CTCGGGGCCA GAGCACGAAA       300

CCCGCATCGG ATCCCCGAGC TCACGCCGGG CGGAGACCAT CGCACACCCG AGGGGCATGA      360

CCGATGGCTG AGTCGGAACA AGCCACGCCC AACATAAGTC TTTAAAAGCG GGCACACGCG      420

TCCCGCCAGT CTCCGGATCC GCCCGCCGGC TTTCCTCGGT CAGACCTCGT TAGCTCCGCC      480

CGCCGCGTGC TCCCTCCTCC CACTCGGGTG AGTCCTAGGC TC                        522
```

(2) INFORMATION FOR SEQ ID NO:17:

(i) SEQUENCE CHARACTERISTICS:
        (A) LENGTH: 297 base pairs
        (B) TYPE: nucleic acid
        (C) STRANDEDNESS: both (D) TOPOLOGY: linear (ii) MOLECULE TYPE: DNA (xi) SEQUENCE DESCRIPTION: SEQ ID NO:17:

ATTTGGGTAC CACCTCTTAA TTAACCTTTC AGAGGAGCTG TTGTGATTTT TAGATGATGA      60

GAAGTTATCT GGTTCCTTCC TCCAGTGAAA ACCAGTCTCC TGATTAAAAA AAAAAAAAAG     120

ACCGTTTCTT TAAAAAGACA ATCAATTCCT TTATGCAGTA GGCTAACATT TGCACTCTGA     180

GAGCTGAAAA CGACATTTTA CTTTTGAGAT TTTCATTCAT ATATATATAT ATATATACAT     240

ATATATATAT ATATATATAT ATATATATAT ATATATATAT ACAAAACACT CCGTGGA       297

(2) INFORMATION FOR SEQ ID NO:18:

(i) SEQUENCE CHARACTERISTICS:
        (A) LENGTH: 52 amino acids
        (B) TYPE: amino acid
        (D) TOPOLOGY: linear (ii) MOLECULE TYPE: protein (ix) FEATURE:
        (D) OTHER INFORMATION: Xaa is any amino acid or unknown.

(xi) SEQUENCE DESCRIPTION: SEQ ID NO:18:

Cys Xaa Xaa Cys Xaa Xaa Xaa Xaa Xaa Xaa Xaa Xaa Xaa Xaa Xaa
 1               5                  10                  15

Xaa Xaa Xaa Xaa Xaa His Xaa Xaa Cys Xaa Xaa Cys Xaa Xaa Cys Xaa
            20                  25                  30

Xaa Xaa Xaa Xaa Xaa Xaa Xaa Xaa Xaa Xaa Xaa Xaa Xaa Xaa Xaa
        35                  40                  45

Cys Xaa Xaa Xaa
    50

(2) INFORMATION FOR SEQ ID NO:19:

(i) SEQUENCE CHARACTERISTICS:
        (A) LENGTH: 79 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:19:

AGTCTCCGGA TCCGCCCGCG GCTTTCCTCG GTCAGACCTC GTTAGCTCCG CCCGCCGCGT      60

GCTCCCTCCT CCCACTCGG                                                  79

(2) INFORMATION FOR SEQ ID NO:20:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:20:

GTGAGTCCTA GGCTC                                                      15

(2) INFORMATION FOR SEQ ID NO:21:

(i) SEQUENCE CHARACTERISTICS:

(A) LENGTH: 215 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:21:

GAGCTCTGTG AGTAAGAGCG ATGTTTCCTC CACGATATGC TAGATAAAAA TCTGGGGGTG      60

GGGGGTAACC AGAAGAGGGA CAAAGCACCT TGTACTAATT GTTTAAATAT TTAATAAAGG     120

TCTCATCAGG AAACCTAATA GAGGTCTGCA CCATTTAATG GTTGTATGGG AATCACGCCT     180

TTAAGGCAAA GATGAGCTTT CTCTGCTACA GACTA                                215

(2) INFORMATION FOR SEQ ID NO:22:

(i) SEQUENCE CHARACTERISTICS:
        (A) LENGTH: 90 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:22:

AAGCATCTGC TAGTACGCAC TGTCTCGTGG CTGAAGCAGC CGGAGGGAAC TCGTAAAACA      60

ACGCATCCTA ATGCATCCTT TGTTCCGCAG                                       90

(2) INFORMATION FOR SEQ ID NO:23:

(i) SEQUENCE CHARACTERISTICS:
        (A) LENGTH: 113 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:23:

CATGCCTGTC TGGGGCGGTG GAAATAAGTG CGGGGCCTGC GGGAGAACCG TGTACCACGC      60

GGAAGAGGTG CAGTGCGATG GGCGGACGTT CCATCGCTGC TGCTTCCTGT GCA            113

(2) INFORMATION FOR SEQ ID NO:24:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:24:

Met Pro Val Trp Gly Gly Gly Asn Lys Cys Gly Ala Cys Gly Arg Thr
 1               5                  10                  15

Val Tyr His Ala Glu Glu Val Gln Cys Asp Gly Arg Thr Phe His Arg
                20                  25                  30

Cys Cys Phe Leu Cys Met
            35

(2) INFORMATION FOR SEQ ID NO:25:

(i) SEQUENCE CHARACTERISTICS:
        (A) LENGTH: 256 base pairs
        (B) TYPE: nucleic acid
        (C) STRANDEDNESS: both (D) TOPOLOGY: linear (ii) MOLECULE TYPE: DNA (xi) SEQUENCE DESCRIPTION: SEQ ID NO:25:

GTGAGTATGG TCCCCTCCCC CTTCAGTTCA CCTCTGGAAG AAAAATAACA ATGCTAGCTA      60

AGAGAAATGG TTTAGAGTGA CGGGGTTTTT TGTTTGTTTG TTTTTTGTTT TAACCGCTGA     120

GTCATCTCTC TAGCCCAATG CGGTGTTTTA TGTCATTGAT CTTAAGACGC TGAGGACTGA     180

GCCAGAGGGA AGACCACCTA GCCCTCAGTT CTGGCCAGTT GGCTTAGCCT TTGTCACCTC     240

TGTCTGTGTC CTCGGG                                                    256

(2) INFORMATION FOR SEQ ID NO:26:

(i) SEQUENCE CHARACTERISTICS:
        (A) LENGTH: 129 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:26:

GTCATTTGGA GGCACCTCTG TTTTAAGTTA AAGCTATATA TATATATATA TATATATATA      60

TATATATATA TATATATATA TATATTCATA TTTTAATGAT GTTTAAAATC TATCTACCCT     120

GGGGCTTAG                                                            129

(2) INFORMATION FOR SEQ ID NO:27:

(i) SEQUENCE CHARACTERISTICS:
        (A) LENGTH: 169 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:27:

TGGTTTGCAG GAAAAATTTA GACAGCACAA CAGTGGCGAT TCATGATGAA GAGATCTACT      60

GCAAATCCTG CTACGGAAAG AAGTATGGAC CAAAAGGCTA TGGTTATGGC CAGGGCGCTG     120

GCACGCTCAA CATGGACCGC GGTGAGAGAC TGGGCATCAA GCCAGAGAG                169

(2) INFORMATION FOR SEQ ID NO:28:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO:28:

Val Cys Arg Lys Asn Leu Asp Ser Thr Thr Val Ala Ile His Asp Glu
 1               5                  10                  15

Glu Ile Tyr Cys Lys Ser Cys Tyr Gly Lys Lys Tyr Gly Pro Lys Gly
                20                  25                  30

Tyr Gly Tyr Gly Gln Gly Ala Gly Thr Leu Asn Met Asp Arg Gly Glu
            35                  40                  45

Arg Leu Gly Ile Lys Pro Glu Ser
        50                  55

(2) INFORMATION FOR SEQ ID NO:29:

(i) SEQUENCE CHARACTERISTICS:
        (A) LENGTH: 448 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:29:

```
GTGAGAGAAT GTTACCCTCT TAAAAGCGGG TAGAACAGCT CCTGTCGCTC AGGCACCAGG      60

AGCCTGCATA TTTAGTTTAA ACTAAGCAAG CAAAATAAAA TGTGACCTCT ACTAAATACT     120

CATATGATTA CTACGACGTT CTGTAACGTC ATAATATTGA CAGTTTTGTA TCTAAAAATC     180

TTAGTAATGA ATGCAGGGAC TTCTAGCCCT GGTTATATAG CATTTTAACT GATATCAGGA     240

AAACATAAAT CTCAAGGAAC TGACTTACTT AATATCCCAT ACGCACTGGA GATCAAATAT     300

CTTGAAATGA GTGTCTGAAT TCTGAGATCG TTCTCATATG ATTAACTGTC CACGGAAAGT     360

CCTTAGTCAC TCTTTCCTCA GGAAATTACA TCCTTCAACT TAGAAATTAA AACCATTTCC     420

TCGTTCTGAT GATTTGAGGG ACAAATCG                                       448
```

(2) INFORMATION FOR SEQ ID NO:30:

(i) SEQUENCE CHARACTERISTICS:
        (A) LENGTH: 306 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:30:

```
AAATGTTTCA CAATATACAT TACCTCTAAA TCTTCCCATC AATGAAAACT AAATTCACAA      60

GACCCCCAAG GCTGTGTTTG TAGCCAGAAC TGGGAAATCA CGGATGCTCT TTCTGCCCTG     120

TCCCCACCTT TCCCAGCAAT AAGCAAGCTC TGTGTGCACG CCCTATGTGC AGTGGTAACC     180

CTGTCTGTCC CTTCCAGCCG GGCCCTGGTC TGGTCTTCCT CTGCGATCAG GTCTAAGGAA     240

TTCCTCCTCC CAGAGGTCTT CTTTAGGACT CAAAACCATG GCCTGCCTTT TAACACACAG     300

ATTAAA                                                               306
```

(2) INFORMATION FOR SEQ ID NO:31:

(i) SEQUENCE CHARACTERISTICS:
        (A) LENGTH: 69 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:31:

```
CGAAGCTCCT GTTAGCTCAG GAGGAACATT TGGAGAAACA CTGCCTCATT TTTTTCTCCG      60

TTCCTCCAG                                                             69
```

(2) INFORMATION FOR SEQ ID NO:32:

(i) SEQUENCE CHARACTERISTICS:
        (A) LENGTH: 130 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:32:

TGCTCAACCT CACAGGCCTA CGACAAATCC AAACACTTCT AAATTTGCCC AGAAATATGG        60

AGGAGCTGAG AAGTGTTCCA GGTGTGGGGA TTCCGTGTAT GCTGCGGAGA AGATCATTGG       120

AGCTGGGAAG                                                              130

(2) INFORMATION FOR SEQ ID NO:33:

(i) SEQUENCE CHARACTERISTICS:
            (A) LENGTH: 43 amino acids
            (B) TYPE: amino acid
            (D) TOPOLOGY: linear (ii) MOLECULE TYPE: peptide (xi) SEQUENCE DESCRIPTION: SEQ ID NO:33:

Ala Gln Pro His Arg Pro Thr Thr Asn Pro Asn Thr Ser Lys Phe Ala
1               5                   10                  15

Gln Lys Tyr Gly Gly Ala Glu Lys Cys Ser Arg Cys Gly Asp Ser Val
            20                  25                  30

Tyr Ala Ala Glu Lys Ile Ile Gly Ala Gly Lys
        35                  40

(2) INFORMATION FOR SEQ ID NO:34:

(i) SEQUENCE CHARACTERISTICS:
            (A) LENGTH: 142 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:34:

GTAGGGCGCT GTCTCTAAGT GGTAACTGCA GCACACACTC ACACACACAC AGGGTGCTGT        60

CTGTCTCTAA CTGGTAACTG TAATAAACAC ACACATACAT ACACAAGCAT ACATAGACAC       120

ACACACACAC ACACACACAT AC                                                142

(2) INFORMATION FOR SEQ ID NO:35:

(i) SEQUENCE CHARACTERISTICS:
            (A) LENGTH: 188 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:35:

CTGCTCCCAG CAAACAGCCC TTTACTGGTG GCTAGAAGAT ATGACAGCAA AGAGGCCAGC        60

TTTCTAGCTG AGCCAAACCG TAGCCTGAGG AGGCTGCTTG TGCGCTGGTT TTCCCAGCCA       120

CTTGCTGCAT CTAGATCGAG CCAAAGGAAA CAAGCCTCTC AATGTCCTAA CTCAGCTGTC       180

TCTTCCAG                                                                188

(2) INFORMATION FOR SEQ ID NO:36:

(i) SEQUENCE CHARACTERISTICS:
            (A) LENGTH: 94 base pairs
            (B) TYPE: nucleic acid
            (C) STRANDEDNESS: both
            (D) TOPOLOGY: linear (ii) MOLECULE TYPE: DNA (xi) SEQUENCE DESCRIPTION: SEQ ID NO:36:

CCCTGGCACA AAAACTGTTT CCGGTGTGCC AAGTGTGGGA AGAGTCTGGA GTCTACAACT    60

CTGACTGAGA AGAAGGCGA AATCTACTGT AAAG    94

(2) INFORMATION FOR SEQ ID NO:37:

(i) SEQUENCE CHARACTERISTICS:
          (A) LENGTH: 32 amino acids
          (B) TYPE: amino acid
          (D) TOPOLOGY: linear (ii) MOLECULE TYPE: peptide (xi) SEQUENCE DESCRIPTION: SEQ ID NO:37:

Pro Trp His Lys Asn Cys Phe Arg Cys Ala Lys Cys Gly Lys Ser Leu
 1               5                  10                  15

Glu Ser Thr Thr Leu Thr Glu Lys Glu Gly Glu Ile Tyr Cys Lys Gly
                20                  25                  30

(2) INFORMATION FOR SEQ ID NO:38:

(i) SEQUENCE CHARACTERISTICS:
          (A) LENGTH: 471 base pairs
          (B) TYPE: nucleic acid
          (C) STRANDEDNESS: both
          (D) TOPOLOGY: linear (ii) MOLECULE TYPE: DNA (xi) SEQUENCE DESCRIPTION: SEQ ID NO:38:

GTAAAAACTC GGTTCTGCTG TCTGTTAGTG TCACCAGAAA GGGAGACATC GTGCACTGTT    60

ACCTTTTGAA AATGAGACCG ACATCTTAGG ACAGTGATTA CTTCTTCCAT TCCTACTGTG   120

TGTGTTAAGT CCACACGGCT GGGGATCTGG CCGAATGGTA AAAGCTTGCC TATGTAGCAC   180

ATTCACAAGG AGGCCACGCT CAGCACGGCC TCCCCAACCT CTGACTTCCT GCTTTAAGCC   240

AAGCATATGA CTACGTGAGG GTGACACACA GAAGGCAGCT GGATTTCAGC CTGCAGCTCA   300

TCACAATCCT AACTTGGATG CCGTGGGAAT TCCTGGACTC GCTTCAAACA AGGATGCTCA   360

TAGCAGAGCC CATTTTATAT CTTAAACTGA CCTCTGCAGA GCCTCCAGTT GGCTTTTAAA   420

TTAATGGCCA TTTGTTAGTG ACCTCTGATT AACTCTCCCT TTCCTTTGTA G    471

(2) INFORMATION FOR SEQ ID NO:39:

(i) SEQUENCE CHARACTERISTICS:
          (A) LENGTH: 283 base pairs
          (B) TYPE: nucleic acid
          (C) STRANDEDNESS: both
          (D) TOPOLOGY: linear (ii) MOLECULE TYPE: DNA (xi) SEQUENCE DESCRIPTION: SEQ ID NO:39:

GGTGCTACGC AAAGAACTTT GGGCCCAAGG GATTTGGCTA TGGTCAAGGG CAGGGGCCC    60

TTGTTCATGC TCAGTAATGG TGTGAACCAG TAAGCACGAC AGAGAATCTC CATTACCAAA   120

CTGCAGATGG CGTTTATGGC GCTCACTACT GTGAAACAGC CAGCACTTGG CACTGGGCAT   180

CACCGAGCTG CCTGTGGGGG CTGGACCGAC AGCGCTGCAC TCTCCCGCCC ACTCACTAGC   240

GTCTAAGAGC ATTCTTTTAC ATTTGAAATA AAATTTTGGC TTG    283

(2) INFORMATION FOR SEQ ID NO:40:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:40:

```
Cys Tyr Ala Lys Asn Phe Gly Pro Lys Gly Phe Gly Tyr Gly Gln Gly
 1               5                  10                  15

Ala Gly Ala Leu Val His Ala Gln
            20
```

(2) INFORMATION FOR SEQ ID NO:41:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:41:

```
Tyr Ala Tyr Thr Cys Tyr Tyr Tyr
                 5
```

(2) INFORMATION FOR SEQ ID NO:42:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:42:

```
Thr Thr Thr Ala Ala Ala
                 5
```

(2) INFORMATION FOR SEQ ID NO:43:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:43:

```
Cys Cys Ala Ala Thr
             5
```

(2) INFORMATION FOR SEQ ID NO:44:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:44:

```
Cys Ala Asn Asn Thr Gly
                 5
```

```
(2) INFORMATION FOR SEQ ID NO:45:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:45:

Gly Gly Gly Arg Asn Thr Tyr Tyr Cys
                 5

(2) INFORMATION FOR SEQ ID NO:46:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:46:

Cys Ala Cys Cys Cys
```